US007947444B2

(12) United States Patent
Moore

(10) Patent No.: US 7,947,444 B2
(45) Date of Patent: May 24, 2011

(54) LEPTIN PROMOTER POLYMORPHISMS AND USES THEREOF

(75) Inventor: Stephen Stewart Moore, Alberta (CA)

(73) Assignee: University of Alberta (CA)

( * ) Notice: Subject to any disclaimer, the term of this patent is extended or adjusted under 35 U.S.C. 154(b) by 314 days.

(21) Appl. No.: 12/115,837

(22) Filed: May 6, 2008

(65) Prior Publication Data

US 2008/0244763 A1    Oct. 2, 2008

Related U.S. Application Data

(62) Division of application No. 11/061,942, filed on Feb. 19, 2005, now abandoned.

(60) Provisional application No. 60/546,456, filed on Feb. 19, 2004.

(51) Int. Cl.
*C12Q 1/68*    (2006.01)
*C12P 19/34*    (2006.01)

(52) U.S. Cl. ............................................ 435/6; 435/91.2

(58) Field of Classification Search ........................ None
See application file for complete search history.

(56) References Cited

U.S. PATENT DOCUMENTS

2008/0096207 A1 *    4/2008 Woodward .......................... 435/6

FOREIGN PATENT DOCUMENTS

WO    WO 03/097876 A    11/2003
WO    WO 2004/083456 A1    9/2004

OTHER PUBLICATIONS

Thisted R.A. 'What is a P-value?' (May 25, 1998) from www.stat.uchicago.edu/~thisted, pp. 1-6.*
Hacker U.T. et al. Gut (May 1997) vol. 40, No. 5, pp. 623-627.*
Buchanan, F.C., et al. Association of a missense mutation in the bovire leptin gene with carcass fat content and leptin mRNA levels. Genet. Sel. Evol. Jan.-Feb. 2002, vol. 34, No. 1, pp. 105-116, ISSN: 0999-193X. See abstract; figure 1; p. 107, lines 23-32; p. 109, lines 5-10; and p. 111, line 2 to p. 112, line 12.
Taniguchi, Y, et al. Genomic structure and promoter analysis of the bovine leptin gene. IUBMB Life. Feb. 2002, vol. 53, No. 2, pp. 131-135, ISSN: 1521-6543. See abstract; figure 1; and p. 133, right column, line 10 to p. 134, left column, line 3.
Liefers, S.C., et al. Association of leptin gene polymorphisms with serum leptin concentration in dairy cows. Mamm. Genome. Sep. 2003, vol. 14, No. 9, pp. 657-663, ISSN: 0938-8990. See abstract; Table 1; and p. 658, left column, lines 24-37, and right column, lines 19-23 and 30-37.
Lagonigro, R., et al. A new mutation in the coding region of the bovine leptin gene associated with feed intyake. Anim. Genet. Oct. 2003, vol. 34, No. 5, pp. 371-374, ISSN: 0268-9146. See the entire document.
Nkrumah, J. D., et al. Association of a single nucleotide polymorphism in the bovine lept8in gene with feed intake, feed efficiency, growth, feeding behaviour, carcass quality and body composition. Canadian Journal of Animal Science. Jun. 2004, vol. 84, pp. 211-219. See the entire document.
Buchanan, F.C., et al. Hot topic: an association between a leptin single nucleotide polymorphism and milk and protein yield. J. Dairy Sci. Oct. 2003, vol. 86, No. 10, pp. 3164-3166, ISSN: 0022-0302. See entire document.
Van Der Lende, T., et al. Leptin gene polymorphisms and their phenotypic associations. Vitamins and Hormones. 2005, vol. 71, pp. 373-404, ISSN: 0083-6729. See the entire document.
Liefers, S. C., et al. Associations between leptin gene polymorphisms and production, live weight, energy balance, feed intake, and fertility in Holstein heifers. J. Dairy Sci. Jun. 2002, vol. 85, No. 6 pp. 1633-1638, ISSN: 0022-0302. See the entire document.
& Database EMBL [Online] Aug. 22, 2001, "Bos Taurus gene for leptin, 5' flanking sequence and exon 1" XP002469562 retrieved from EBI accession No. EM_OM: AB070368 Database accession No. AB070368.
Database EMBL [Online] Oct. 8, 2002, "Bos Taurus leptin gene, exon 2 and partial cds." XP002469502 retrieved from EBI accession No. EM_OM: AY138588 Database accession No. AY138588.
Schenkel F. S. et al.: "Association of single nucleotide polymorphisms in the leptin gene with carcass and meat quality traits of beef cattle" Journal of Animal Science, vol. 83, No. 9, Sep. 2005, pp. 2009-2020, XP002469500 ISSN: 0021-8812.
Oksanen L et al.: "Novel polymorphism of the human ob gene promoter in lean and morbidly obese subjects." International Journal of Obesity and Related Metabolic Disorders: Jornal of the International Association for the Study of Obesity Jun. 1997, vol. 21, No. 6, b, pp. 489-494, XP002469501 ISSN: 0307-0565.

* cited by examiner

*Primary Examiner* — Stephen Kapushoc
(74) *Attorney, Agent, or Firm* — Judy Jarecki-Black; Chad Kitchen; Merial Limited

(57) ABSTRACT

The present invention relates to single nucleotide polymorphisms (SNPs) in the leptin promoter, and to methods for the identification of animals carrying specific alleles of these SNPs that are associated with circulating leptin levels, feed intake, growth rate, body weight, carcass merit and carcass composition. The present invention provides oligonucleotides that can be used as primers and/or probes to amplify and/or detect these SNPs, and provides methods for selecting and grouping animals, in particular bovines, according to genotype.

2 Claims, 10 Drawing Sheets

Figure1 (SEQ. ID NO.: 1)
*Bos Taurus* gene for leptin; 5' Flanking sequence and Exon 1

```
   1 gaattcaaca attctattta tcaagaaatc tcccacaaat atactcacac tgtgctccaa
  61 taagtacttt tgagtctatt aattaacaac attatgtatc taacattatg gttagattga
 121 ttatggtgca tctgtgaaat gaaacatacg ctgactctaa aatgattggc acaatcctgt
 181 gtattggtaa gaaattgtat tctagatata ctaggtgaaa gaagtgagat taataatggt
 241 taaaattggg caatggtaca tggacatttg taatgccatt tttccttata agtgtattgt
 301 ggagatttaa atttttccaa aaaaaaaaat gtggaggcag ggggcaagaa cattagtgtg
 361 aataatatga cattatttaa atgcccttaa atatatattt tttaattaat ttatttattt
 421 tttctatgct gggtcttcat tgcaatgtgc aagcttctca ctgtggcagc ttctcctgtt
 481 gtggagcata ggctccaggt gcccagggac tcagcggttg caacacacag gctctagagc
 541 ttgggctcgg gagccgtgtc acacggcctt tgttgctccc agcatgtgga atcttcctca
 601 accagggacc gatcccgcgt ccctgcactg gcaggcggat tctcatccac tgtaccacca
 661 aggaaggcct gcacactttt tttttaagg aaatggatat atgaaggaca gaaaaagaat
 721 atccatggaa ggatacacca taaactgaga agaacaacta cttctaggga aaaaaggact
 781 ggggagagac tgagttttca tatctttgtt ccttttgaat tttaagaaaa ataatacatt
 841 attctaacac aacattgtaa agcaattata cttcaataaa aaattaaaag taaaaatact
 901 ttattatata ataatatata attataaat aatataaaca ttcagttcag ttcagttcac
 961 ttcagtcgct cagtcgtgtc cgactctttt cgaccccatg aatcgcagca caccaggcct
1021 ccctgtccat caccaactcc cggagttcac ccagactcat agtaatatat aataatttat
1081 tttaaaataa ttattaatca acacgaaatg taaaaaatag gtaggtgatg ggtagatagg
1141 cagacgggca gtccacacac tcacatgtgg tctcaagtgc tacttggtgt tcaggcaata
1201 actctggtcc caatctgacc tctgaccctt aaaaaggtga tggtaagaca agtaacctga
1261 ggctgccagg gcccctgcct atgagctaag actctgctta gaaccaagtt acaaagatgt
1321 tgcagacaag aaaaatttgg tcgtagtgga tgctactgcc tctatttgaa aaacaacaca
1381 aacatttccg gggggggggg gaggcggaga ggaggaaaga ttttcttcaa aatgtaattt
1441 cattgtagac acttctttaa aagaaacatt tctttatttg acagttccag gccttagttt
1501 cagcaggcag gatgtttagt cgcagcatga gaactcttag ctgcggcatg cgggacccag
1561 ttcagttccc tgaccagata tcgaacctgg ggccctgca tttggaagca gggagtctta
1621 gccactggac caccagggaa gtccctgta gatgtttta tgaaaagcag aaaagcacaa
1681 agaagagctt aaagattcct gatcctactc ccaatagtga taatgtatat tttggtgtga
1741 gagtgtgtgt attgattgga atgtgtgtga tcagaaaaca cataccattt tataatccgt
1801 tctttccagc tcacaaaata aagttatttt cctacatcat taaatattac tttacaacat
1861 aattttaat gtgtgcatat tgctgctatg tgattttcaa taacttacta atttcctatg
1921 ctgaacattt agttgttgtc caacctttt agtggccatg taattataaa tcatggtcaa
1981 tgctaacaat ttctgacctc acaaacatat agtacaaat ccttcctttc ttcaatagat
2041 aattattaaa agcaaaacaa ccaggctcaa acaaagcaat tataaaatat cttaaaaag
2101 acattgggta aaattcaaat gcagactagc tcatgatgtt aaagaattac tcttgtgtgg
2161 taatggtctt gtgatagaga tagaaatgct tccttatttt tcagataaac acttaagtat
2221 ttaaggatga aacgccctga tgtttgtaat ttgctttaga atattttagc caaaagaatt
2281 aatgatgcaa atatgcaaaa agagtacgtt aaacctaaat ttgcgatttt catttaaaaa
2341 tatatcttaa aaatgaaaat cttcgtgcaa cgcacggggc tatcaatgtg ggatacagat
2401 gtgaacaaaa cggacccgtg tgggactcgg cggagcacac agatttgcg ggagcacgtt
2461 cccgttagga agtctctgat gcaatacgac cggtgcccctt caggacctgt gagactgact
2521 ttccttaccc ctccacacca tcatcaaggc aggtgtgatt ttccaggcca ggcctacggc
2581 cgggtttccc cggggggcca gagccgtcgg gtcttgccgc ccagcggagc tggctgctcc
2641 ggcctcactg tcggggcgcc accgccccca gccggctcag aggaacccct caccgccacc
2701 ctgtcccagg cggccttttcc ccgaggcccg agggtcagat cctggggcca cctcgaggat
2761 ttctcacacc tgcccagcca cccccagctt ttcaggtgat accggagggt gggcgtgggg
2821 ctcctggcgc atccgagtcc ctccctggag tccccgaccg cggccgcccg gcccgacgct
2881 gcccgccgc cccgcagggc gggagccggc gctgcgggtg cgccccggcc agccgggcag
2941 ttgcgcaagt tgtgcttcgg cggctataag aggggcgggc aggcatggag ccccggaggg
3001 atcgaggaat cgcggcgcca gcagcggcga ggtaagtgcc cggctctctc ct
```

FIGURE 2. (SEQ. ID NO.:2)
UASMS1 SNP (C/T substitution at position 207)

```
   1 gaattcaaca attctattta tcaagaaatc tcccacaaat atactcacac tgtgctccaa
  61 taagtacttt tgagtctatt aattaacaac attatgtatc taacattatg gttagattga
 121 ttatggtgca tctgtgaaat gaaacatacg ctgactctaa aatgattggc acaatcctgt
 181 gtattggtaa gaaattgtat tctagaCata ctaggtgaaa gaagtgagat taataatggt
 241 taaaattggg caatggtaca tggacatttg taatgccatt tttccttata agtgtattgt
 301 ggagatttaa atttttccaa aaaaaaaaat gtggaggcag ggggcaagaa cattagtgtg
 361 aataaatatga cattatttaa atgcccttaa atatatattt tttaattaat ttatttattt
 421 tttctatgct gggtcttcat tgcaatgtgc aagcttctca ctgtggcagc ttctcctgtt
 481 gtggagcata ggctccaggt gcccagggac tcagcggttg caacacacag gctctagagc
 541 ttgggctcgg gagccgtgtc acacggcctt tgttgctccc agcatgtgga atcttcctca
 601 accagggacc gatcccgcgt ccctgcactg gcaggcggat tctcatccac tgtaccacca
 661 aggaaggcct gcacactttt tttttaagg aaatggatat atgaaggaca gaaaaagaat
 721 atccatggaa ggatacacca taaactgaga agaacaacta cttctaggga aaaaaggact
 781 ggggagagac tgagtttttca tatctttgtt ccttttgaat tttaagaaaa ataatacatt
 841 attctaacac aacattgtaa agcaattata cttcaataaa aaattaaaag taaaaatact
 901 ttattatata ataatatata attataaatat aatataaaca ttcagttcag ttcagttcac
 961 ttcagtcgct cagtcgtgtc cgactctttt cgacccatg aatcgcagca caccaggcct
1021 ccctgtccat caccaactcc cggagttcac ccagactcat agtaatatat aataatttat
1081 tttaaaataa ttattaatca acacgaaatg taaaaaatag gtaggtgatg ggtagatagg
1141 cagacgggca gtccacacac tcacatgtgg tctcaagtgc tacttggtgt tcaggcaata
1201 actctggtcc caatctgacc tctgacccctt aaaaaggtga tggtaagaca agtaacctga
1261 ggctgccagg gcccctgcct atgagctaag actctgctta gaaccaagtt acaaagatgt
1321 tgcagacaag aaaaatttgg tcgtagtgga tgctactgcc tctatttgaa aaacaacaca
1381 aacatttccg ggggggggg gaggcggaga ggaggaaaga ttttcttcaa aatgtaattt
1441 cattgtagac acttctttaa aagaaacatt tctttatttg acagttccag gccttagttt
1501 cagcaggcag gatgtttagt cgcagcatga gaactcttag ctgcggcatg cgggacccag
1561 ttcagttccc tgaccagata tcgaacctgg ggcccctgca tttggaagca gggagtctta
1621 gccactggac caccagggaa gtccctgta gatgttttta tgaaaagcag aaaagcacaa
1681 agaagagctt aaagattcct gatcctactc ccaatagtga taatgtatat tttggtgtga
1741 gagtgtgtgt attgattgga atgtgtgtga tcagaaaaca cataccattt tataatccgt
1801 tctttccagc tcacaaaata aagttatttt cctacatcat taaatattac tttacaacat
1861 aatttttaat gtgtgcatat tgctgctatg tgattttcaa taacttacta atttcctatg
1921 ctgaacattt agttgttgtc caaccttttt agtggccatg taattataaa tcatggtcaa
1981 tgctaacaat ttctgacctc acaaacatat agtacaatat ccttccttc ttcaatagat
2041 aattattaaa agcaaaacaa ccaggctcaa acaaagcaat tataaaatat ctttaaaaag
2101 acattgggta aaattcaaat gcagactagc tcatgatgtt aaagaattac tcttgtgtgg
2161 taatggtctt gtgatagaga tagaaatgct tccttatttt tcagataaac acttaagtat
2221 ttaaggatga aacgccctga tgtttgtaat ttgctttaga atatttagc caaaagaatt
2281 aatgatgcaa atatgcaaaa agagtacgtt aaacctaaat ttgcgatttt catttaaaaa
2341 tatatcttaa aaatgaaaat cttcgtgcaa cgcacggggc tatcaatgtg ggatacagat
2401 gtgaacaaaa cggacccgtg tgggactcgg cggagcacac agatttgcg ggagcacgtt
2461 cccgttagga agtctctgat gcaatacgac cggtgccctt caggacctgt gagactgact
2521 ttccttaccc ctccacacca tcatcaaggc aggtgtgatt ttccaggcca ggcctacggc
2581 cgggtttccc cggggggccca gagccgtcgg gtcttgccgc ccagcggagc tggctgctcc
2641 ggcctcactg tcggggcgcc accgccccca gccggctcag aggaaccct caccgccacc
2701 ctgtcccagg cggcctttcc ccgaggcccg agggtcagat cctggggcca cctcgaggat
2761 ttctcacacc tgcccagcca ccccagctt tcaggtgat accggagggt gggcgtgggg
2821 ctcctggcgc atccgagtcc ctccctggag tccccgaccg cggccgcccg gccgacgct
2881 gccccgccgc cccgcagggc gggagccggc gctgcgggtg cgccccggcc agccgggcag
2941 ttgcgcaagt tgtgcttcgg cggctataag aggggcgggc aggcatggag ccccggaggg
3001 atcgaggaat cgcggcgcca gcagcggcga ggtaagtgcc cggctctctc ct
```

FIGURE 3. (SEQ. ID NO.:3)
UASMS2 SNP (C/T substitution at position 528)

```
   1 gaattcaaca attctattta tcaagaaatc tcccacaaat atactcacac tgtgctccaa
  61 taagtactt tgagtctatt aattaacaac attatgtatc taacattatg gttagattga
 121 ttatggtgca tctgtgaaat gaaacatacg ctgactctaa aatgattggc acaatcctgt
 181 gtattggtaa gaaattgtat tctagatata ctaggtgaaa gaagtgagat taataatggt
 241 taaaattggg caatggtaca tggacatttg taatgccatt tttccttata agtgtattgt
 301 ggagatttaa atttttccaa aaaaaaaaat gtggaggcag ggggcaagaa cattagtgtg
 361 aataaatga cattatttaa atgcccttaa atatatattt tttaattaat ttatttattt
 421 tttctatgct gggtcttcat tgcaatgtgc aagcttctca ctgtggcagc ttctcctgtt
 481 gtggagcata ggctccaggt gcccagggac tcagcggttg caacacaTag gctctagagc
 541 ttgggctcgg gagccgtgtc acacggcctt tgttgctccc agcatgtgga atcttcctca
 601 accagggacc gatcccgcgt ccctgcactg gcaggcggat tctcatccac tgtaccacca
 661 aggaaggcct gcacactttt tttttaagg aaatggatat atgaaggaca gaaaaagaat
 721 atccatgaa ggatacacca taaactgaga agaacaacta cttctaggga aaaaaggact
 781 ggggagagac tgagttttca tatctttgtt cctttgaat tttaagaaaa ataatacatt
 841 attctaacac aacattgtaa agcaattata cttcaataaa aaattaaaag taaaaatact
 901 ttattatata ataatatata attataatat aatataaaca ttcagttcag ttcagttcac
 961 ttcagtcgct cagtcgtgtc cgactctttt cgacccatg aatcgcagca caccaggcct
1021 ccctgtccat caccaactcc cggagttcac ccagactcat agtaatatat aataatttat
1081 tttaaaataa ttattaatca acacgaaatg taaaaaatag gtaggtgatg ggtagatagg
1141 cagacgggca gtccacacac tcacatgtgg tctcaagtgc tacttggtgt tcaggcaata
1201 actctggtcc caatctgacc tctgaccctt aaaaaggtga tggtaagaca agtaacctga
1261 ggctgccagg gcccctgcct atgagctaag actctgctta gaaccaagtt acaagatgt
1321 tgcagacaag aaaaatttgg tcgtagtgga tgctactgcc tctatttgaa aaacaacaca
1381 aacatttccg ggggggggg gaggcggaga ggaggaaaga tttcttcaa aatgtaattt
1441 cattgtagac acttctttaa aagaaacatt tctttatttg acagttccag gccttagttt
1501 cagcaggcag gatgtttagt cgcagcatga gaactcttag ctgcggcatg cgggacccag
1561 ttcagttccc tgaccagata tcgaacctgg ggccctgca tttggaagca gggagtctta
1621 gccactggac caccagggaa gtccctgta gatgtttta tgaaaagcag aaaagcacaa
1681 agaagagctt aaagattcct gatcctactc ccaatagtga taatgtatat tttggtgtga
1741 gagtgtgtgt attgattgga atgtgtgtga tcagaaaaca cataccattt tataatccgt
1801 tctttccagc tcacaaaata aagttatttt cctacatcat taaatattac tttacaacat
1861 aattttaat gtgtgcatat tgctgctatg tgattttcaa taacttacta atttcctatg
1921 ctgaacattt agttgttgtc caaccttttt agtggccatg taattataaa tcatggtcaa
1981 tgctaacaat ttctgacctc acaaacatat agtacaatat ccttccttc ttcaatagat
2041 aattattaaa agcaaaacaa ccaggctcaa acaaagcaat tataaaatat ctttaaaaag
2101 acattgggta aaattcaaat gcagactagc tcatgatgtt aaagaattac tcttgtgtgg
2161 taatggtctt gtgatagaga tagaaatgct tccttatttt tcagataaac acttaagtat
2221 ttaaggatga aacgccctga tgtttgtaat ttgctttaga atattttagc caaaagaatt
2281 aatgatgcaa atatgcaaaa agagtacgtt aaacctaaat ttgcgatttt catttaaaaa
2341 tatatcttaa aaatgaaaat cttcgtgcaa cgcacggggc tatcaatgtg ggatacagat
2401 gtgaacaaaa cggaccgtg tgggactcgg cggagcacac agatttgcg ggagcacgtt
2461 cccgttagga agtctctgat gcaatacgac cggtgccctt caggacctgt gagactgact
2521 ttccttaccc ctccacacca tcatcaaggc aggtgtgatt ttccaggcca ggcctacggc
2581 cgggtttccc cggggggccca gagccgtcgg gtcttgccgc ccagcggagc tggctgctcc
2641 ggcctcactg tcggggcgcc accgccccca gccggctcag aggaaccct caccgccacc
2701 ctgtcccagg cggcctttcc ccgaggcccg aggtcagat cctggggcca cctcgaggat
2761 ttctcacacc tgcccagcca ccccagctt ttcaggtgat accggagggt gggcgtgggg
2821 ctcctggcgc atccgagtcc ctccctggag tccccgaccg cggccgcccg gcccgacgct
2881 gccccgccgc ccgcagggc gggagccggc gctgcgggtg cgccccggcc agccgggcag
2941 ttgcgcaagt tgtgcttcgg cggctataag aggggcgggc aggcatggag ccccggaggg
3001 atcgaggaat cgcggcgcca gcagcggcga ggtaagtgcc cggctctctc ct
```

FIGURE 4: (SEQ. ID NO.:4)
UASMS3 SNP (C/G substitution at position 1759

```
   1 gaattcaaca attctattta tcaagaaatc tcccacaaat atactcacac tgtgctccaa
  61 taagtactt tgagtctatt aattaacaac attatgtatc taacattatg gttagattga
 121 ttatggtgca tctgtgaaat gaaacatacg ctgactctaa aatgattggc acaatcctgt
 181 gtattggtaa gaaattgtat tctagatata ctaggtgaaa gaagtgagat taataatggt
 241 taaaattggg caatggtaca tggacatttg taatgccatt tttccttata agtgtattgt
 301 ggagatttaa atttttccaa aaaaaaaaat gtggaggcag ggggcaagaa cattagtgtg
 361 aataatatga cattatttaa atgcccttaa atatatattt tttaattaat ttatttattt
 421 tttctatgct gggtcttcat tgcaatgtgc aagcttctca ctgtggcagc ttctcctgtt
 481 gtggagcata ggctccaggt gcccagggac tcagcggttg caacacacag gctctagagc
 541 ttgggctcgg gagccgtgtc acacggcctt tgttgctccc agcatgtgga atcttcctca
 601 accagggacc gatcccgcgt ccctgcactg gcaggcggat tctcatccac tgtaccacca
 661 aggaaggcct gcacactttt tttttaagg aaatggatat atgaaggaca gaaaaagaat
 721 atccatggaa ggatacacca taaactgaga agaacaacta cttctaggga aaaaaggact
 781 ggggagagac tgagttttca tatcttgtt ccttttgaat tttaagaaaa ataatacatt
 841 attctaacac aacattgtaa agcaattata cttcaataaa aaattaaaag taaaaatact
 901 ttattatata ataatatata attataatat aatataaaca ttcagttcag ttcagttcac
 961 ttcagtcgct cagtcgtgtc cgactctttt cgaccccatg aatcgcagca caccaggcct
1021 ccctgtccat caccaactcc cggagttcac ccagactcat agtaatatat aataatttat
1081 tttaaaataa ttattaatca acacgaaatg taaaaaatag gtaggtgatg ggtagatagg
1141 cagacgggca gtccacacac tcacatgtgg tctcaagtgc tacttggtgt tcaggcaata
1201 actctggtcc caatctgacc tctgacccctt aaaaggtga tggtaagaca agtaacctga
1261 ggctgccagg gcccctgcct atgagctaag actctgctta gaaccaagtt acaaagatgt
1321 tgcagacaag aaaaatttgg tcgtagtgga tgctactgcc tctatttgaa aaacaacaca
1381 aacatttccg gggggggggg gaggcggaga ggaggaaaga ttcttcaa aatgtaattt
1441 cattgtagac acttctttaa aagaaacatt tctttatttg acagttccag gccttagttt
1501 cagcaggcag gatgtttagt cgcagcatga gaactcttag ctgcggcatg cgggacccag
1561 ttcagttccc tgaccagata tcgaacctgg ggccctgca tttggaagca gggagtctta
1621 gccactggac caccagggaa gtccctgta gatgttttta tgaaaagcag aaaagcacaa
1681 agaagagctt aaagattcct gatcctactc ccaatagtga taatgtatat tttggtgtga
1741 gagtgtgtgt attgattgCa atgtgtgtga tcagaaaaca cataccattt tataatccgt
1801 tctttccagc tcacaaaata aagttattt cctacatcat taaatattac tttacaacat
1861 aattttaat gtgtgcatat tgctgctatg tgattttcaa taacttacta atttcctatg
1921 ctgaacattt agttgttgtc caacctttt agtggccatg taattataaa tcatggtcaa
1981 tgctaacaat ttctgacctc acaaacatat agtacaatat ccttccttc ttcaatagat
2041 aattattaaa agcaaaacaa ccaggctcaa acaaagcaat tataaaatat ctttaaaaag
2101 acattgggta aaattcaaat gcagactagc tcatgatgtt aaagaattac tcttgtgtgg
2161 taatggtctt tgtatagaga tagaaatgct tccttatttt tcagataaac acttaagtat
2221 ttaaggatga aacgccctga tgtttgtaat ttgctttaga atattttagc caaaagaatt
2281 aatgatgcaa atatgcaaaa agagtacgtt aaacctaaat ttgcgatttt catttaaaaa
2341 tatatcttaa aaatgaaaat cttcgtgcaa cgcacggggc tatcaatgtg ggatacagat
2401 gtgaacaaaa cggacccgtg tgggactcgg cggagcacac agatttgcg ggagcacgtt
2461 cccgttagga agtctctgat gcaatacgac cggtgcccctt caggacctgt gagactgact
2521 ttccttaccc ctccacacca tcatcaaggc aggtgtgatt ttccaggcca ggcctacggc
2581 cgggtttccc cggggggccca gagccgtcgg gtcttgccgc ccagcggagc tggctgctcc
2641 ggcctcactg tcggggcgcc accgccccca gccggctcag aggaacccct caccgccacc
2701 ctgtcccagg cggcctttcc ccgaggcccg agggtcagat cctggggcca cctcgaggat
2761 ttctcacacc tgcccagcca ccccccagctt ttcaggtgat accggagggt gggcgtgggg
2821 ctcctggcgc atccgagtcc ctccctggag tccccgaccg cggccgcccg gcccgacgct
2881 gccccgccgc ccgcagggc gggagccggc gctgcgggtg cgccccggcc agccgggcag
2941 ttgcgcaagt tgtgcttcgg cggctataag aggggcgggc aggcatggag ccccggaggg
3001 atcgaggaat cgcggcgcca gcagcggcga ggtaagtgcc cggctctctc ct
```

Figure 5 (SEQ ID NO: 5)
*Bos taurus* leptin gene, exon 2 and partial coding sequence

```
  1 gattccgccg cacctctccc caggggagtg cctttcatta ctgtcatttc tagacaatga
 61 attgtctttg aggagatgat agccatggca gacagcaaat cttgttgtta tccgcatctg
121 aagacctgga tgcgggtggt aacggagcac gtgggtgttc tcggagatcg acgatgtgcc
181 acgtgtggtt tcttctgttt tcaggcccca gaagcccatc ccgggaagga aaatgcgctg
241 tggacccctg tttcgattcc tgtggctttg gccctatctg tcttacgtgg aggctgtgcc
301 catctgcaag gtccaggatg acaccaaaac cctcatcaag acaattgtca ccaggatcaa
361 tgacatctca cacacggtag ggagggactg ggagacgagg tagaaccgtg gccatcccgt
421 gggggacccc agaggctggc ggaggaggct gtgcagcctt gcacagg
```

Figure 6 (SEQ ID NO: 6)
EXON2-FB SNP (C/T substitution at position 305)

```
  1 gattccgccg cacctctccc caggggagtg cctttcatta ctgtcatttc tagacaatga
 61 attgtctttg aggagatgat agccatggca gacagcaaat cttgttgtta tccgcatctg
121 aagacctgga tgcgggtggt aacggagcac gtgggtgttc tcggagatcg acgatgtgcc
181 acgtgtggtt tcttctgttt tcaggcccca gaagcccatc ccgggaagga aaatgcgctg
241 tggacccctg tttcgattcc tgtggctttg gccctatctg tcttacgtgg aggctgtgcc
301 catcCgcaag gtccaggatg acaccaaaac cctcatcaag acaattgtca ccaggatcaa
361 tgacatctca cacacggtag ggagggactg ggagacgagg tagaaccgtg gccatcccgt
421 gggggacccc agaggctggc ggaggaggct gtgcagcctt gcacagg
```

LEPTIN PROMOTER POLYMORPHISMS AND USES THEREOF

RELATED APPLICATIONS/PATENTS & INCORPORATION BY REFERENCE

This application is a divisional of U.S. application Ser. No. 11/061,942, filed Feb. 19, 2005 now abandoned, which claims priority to provisional U.S. application Ser. No. 60/546,456 filed Feb. 19, 2004, the contents of which are hereby expressly incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein cited references"), as well as each document or reference cited in each of the herein-cited references (including any manufacturer's specifications, instructions, etc.), is hereby expressly incorporated herein by reference.

FIELD OF THE INVENTION

The present invention relates to single nucleotide polymorphisms in the leptin or ob gene, and to the association of these SNPs with certain traits that are economically important in livestock species, such as circulating leptin levels, feed intake, growth rate, body weight, carcass merit and carcass composition. Three novel SNPs located in the promoter of leptin gene promoter are described. The present invention provides primers and probes useful in the detection of these novel SNPs, and methods of identifying and grouping animals based on their genotype.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals with an advantage for an inheritable trait of circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

Leptin, the hormone product of the ob (obese) gene, has been shown to be predominantly synthesized and expressed in adipose tissues (Zhang, Y., R. Proenca, M. Maffei, M. Barone, L. Leopold, and J. M. Friedman (1994) Positional cloning of the mouse obesity gene and its human homologue, Nature 372: 425-432; Ji, S., G. M. Willis, R. R. Scott, and M. E. Spurlock. 1998. Partial cloning and expression of the bovine leptin gene, Anim. Biotechnol. 9: 1-4). It functions as a potent physiological signal in the regulation of body weight, energy expenditure, feed intake, adiposity, fertility and immune functions (Houseknecht, K. L., Baile, C. A., Matteri, R. L. and Spurlock, M. E. (1998) The biology of leptin: a review. *Journal of Animal Science* 76: 1405-1420; Lord, G. M., G. Matarese, J. K. Howard, R. J. Baker, S. R. Bloom, and R. I. Lechler (1998) Leptin modulates the T-cell immune response and reverses starvation-unduced immunosuppression. Nature 394: 897-900; Garcia, M. R., M. Amstalden, S. W. Williams, R. L. Stanko, C. D. Morrison, D. H. Keisler, S. E. Nizielski, and G. L. Williams (2002) Serum leptin and its adipose gene expression during pubertal development, the estrous cycle, and different seasons in cattle. J. Anim. Sci. 80: 2158-2167). Leptin has been proposed as one of the major control factors contributing to the phenotypic and genetic variation in the performance and efficiency of cattle.

Polymorphisms in the coding regions of the leptin gene in cattle have been associated with milk yield and composition (Liefers, S. C., te Pas, M. F. W., Veerkamp, R. F. and van der Lende, T. (2002) Associations between leptin gene polymorphisms and production, liveweight, energy balance, feed intake and fertility in Holstein heifers. *Journal of Dairy Science* 85:1633-1638), feed intake (Liefers et al., 2002; Lagonigro, R., P. Wiener, F. Pilla, J. A. Woolliams, and J. L. Williams. 2003. A new mutation in the coding region of the bovine leptin gene associated with feed intake. Anim. Genet. 34: 371-374), and body fat (Buchanan, F. C., Fitzsimmons, C. J., Van Kessel, A. G., Thue, T. D., Winkelman-Sim, C. and Schmutz, S. M. (2002) Association of a missense mutation in the bovine leptin gene with carcass fat content and leptin mRNA levels, Genet. Sel. Evol. 34: 105-116; Lagonigro et al., (2003)). However, it would appear that polymorphisms located in the promoter region of the leptin gene (i.e. the region of the gene that regulates the level of leptin expression through its associated enhancer and silencer elements) may have a stronger effect on the regulation of these economically important traits, and therefore be of greater predictive value.

In the present invention it has surprisingly been shown that three previously unknown single nucleotide polymorphisms (SNPs) in the promoter region of the leptin gene, and one previously known SNP in exon 2 of the leptin gene, are strongly associated with several of these economically important traits in cattle. To the best of our knowledge, the genetic markers of the present invention are the first to be identified that show a direct relationship with body weight and feed intake.

OBJECT AND SUMMARY OF THE INVENTION

The present invention relates generally to three previously unknown single nucleotide polymorphisms (SNPs) in the promoter of the leptin or ob gene (SEQ ID NO: 1), and to one previously known SNP in exon 2 of ob gene (SEQ ID NO: 5), and to the association of each of these SNPs with certain traits that are of significant economic importance in livestock species, such as circulating leptin levels, feed intake, growth rate, body weight, carcass merit and carcass composition in livestock species. The three SNPs located in the leptin gene promoter are named UASMS1, UASMS2, and UASMS3.

These three SNPs, in the context of the ob gene promoter sequence, are can be seen in SEQ ID NO: 2, SEQ ID NO: 3, and SEQ ID NO: 4, respectively. The SNP located in exon 2 of the leptin gene is named EXON2-FB, and can seen in the context of exon 2 of the ob gene in SEQ ID NO: 6.

In one aspect the present invention provides methods for grouping animals according to genotype wherein the animals of each sub-group have a similar polymorphism in the leptin gene. Such methods comprise determining the genotype of each animal to be subgrouped by determining the presence of a SNP in the leptin gene, wherein the SNP is selected from the group consisting of UASMS1, UASMS2, UASMS3 and EXON2-FB, and wherein individual animals are placed into sub-groups where each animal in a subgroup has a similar polymorphism in the leptin gene. In a preferred embodiment the animal to be grouped is a bovine, and the leptin gene is the bovine leptin gene.

In another embodiment, the present invention provides methods for identifying animals having desirable traits relating to circulating leptin levels, feed intake, growth rate, body weight, carcass merit and carcass composition, as compared to the general population of animals of that species. Such methods comprise determining the presence of a SNP in the leptin gene of the animal, wherein the polymorphism is selected from the group consisting of UASMS1, UASMS2, UASMS3, and EXON2-FB, and wherein the presence of either the UASMS1, UASMS2, UASMS3 or EXON2-FB SNP is indicative of a desirable trait relating to circulating leptin levels, feed intake, growth rate, body weight, carcass merit and carcass composition. In a preferred embodiment the animal to be grouped is a bovine, and the leptin gene is the bovine leptin gene.

In a further embodiment the present invention provides isolated oligonucleotide probes that are useful in the detection of the UASMS1, UASMS2, UASMS3, and EXON2-FB SNPs in the ob gene. The present invention advantageously provides oligonucleotide probes for detection of the two alternative alleles of each SNP. For example, in the case of the UASMS1 polymorphism, which constitutes a C to T substitution at nucleotide position 207 of the ob gene promoter, the present invention provides oligonucleotide probes that can be used to detect and distinguish between the C-containing allele and the T-containing allele. In the case of the UASMS2 polymorphism, which constitutes a C to T substitution at nucleotide position 528 of the ob gene promoter, the present invention provides oligonucleotide probes that can be used to detect and distinguish between the C-containing allele and the T-containing allele. In the case of the UASMS3 polymorphism, which constitutes a C to G substitution at nucleotide position 1759 of the ob gene promoter, the present invention provides oligonucleotide probes that can be used to detect and distinguish between the C-containing allele and the G-containing allele. Similarly, in the case of the EXON2-FB polymorphism, which constitutes a C to T substitution at nucleotide position 305 of exon 2 of the ob gene, the present invention provides oligonucleotide probes that can be used to detect and distinguish between the C-containing allele and the T-containing allele. In a preferred embodiment, the oligonucleotide probes of the present invention are labeled with a detectable moiety, such as for example, digoxigenin-dUTP, biotin, fluorescent moieties, chemiluminescent moieties, electrochemiluminescent moieties and radioactive moieties.

In a further embodiment the present invention provides isolated primers and primer pairs that are useful in the amplification of fragments of the ob gene that span the UASMS1, UASMS2, UASMS3, and EXON2-FB SNPs. In one embodiment fragments of the ob gene that are amplified using such primers are subsequently detected using the oligonucleotide probes of the present invention.

The oligonucleotide probes and primers described herein are useful for identifying animals having SNPs associated with desirable traits relating to circulating leptin levels, feed intake, growth rate, body weight, carcass merit and carcass composition, as compared to the general population of animals of that species. Once individual animals possessing these SNPs have been identified, the animals can then be grouped according to genotype, wherein the animals of each sub-group have a similar polymorphism in the leptin gene. The present invention also advantageously provides compositions and kits comprising the oligonucleotide probes and primers described herein. These and other embodiments are disclosed or are obvious from and encompassed by, the following Detailed Description.

BRIEF DESCRIPTION OF THE DRAWINGS

In the following Detailed Description and Examples reference will be made to the accompanying drawings, incorporated herein by reference, wherein:

FIG. 1 illustrates the nucleotide sequence for the 5' flanking promoter region and exon 1 of the "wild type" bovine ob gene. This "wild type" sequence has GenBank accession number AB070368 (Taniguchi et al. *IUBMB Life* Vol 53, p 131-135 (2002)), and is designated herein as SEQ ID NO. 1.

FIG. 2 illustrates the nucleotide sequence the UASMS1 single nucleotide polymorphism in the bovine ob gene promoter (SEQ ID NO. 2). This polymophic sequence differs from that of the "wild type" bovine ob gene sequence (SEQ ID NO. 1) in that nucleotide position 207 has a cytosine to thymine substitution.

FIG. 3 illustrates the nucleotide sequence the UASMS2 single nucleotide polymorphism of the bovine ob gene (SEQ ID NO. 3). This polymophic sequence differs from that of the "wild type" bovine ob gene sequence (SEQ ID NO. 1) in that nucleotide position 528 has a cytosine to thymine substitution.

FIG. 4 illustrates the nucleotide sequence the UASMS3 single nucleotide polymorphism of the bovine ob gene (SEQ ID NO. 4). This polymorphic sequence differs from that of the "wild type" bovine ob gene sequence (SEQ ID NO. 1) in that nucleotide position 1759 has a cytosine to guanine substitution.

FIG. 5 illustrates the nucleotide sequence for the exon 2 of the "wild type" bovine ob gene (SEQ ID NO. 5). This "wild type" exon 2 sequence has GenBank accession number AY138588.

FIG. 6 illustrates the nucleotide sequence for the EXON2-FB single nucleotide polymorphism of the bovine ob gene (SEQ ID NO. 6). This polymorphic sequence differs from that of the "wild type" bovine ob gene sequence (SEQ ID NO. 5) in that nucleotide position 305 has a cytosine to thymine substitution.

DETAILED DESCRIPTION i. Definitions

Figure 7:
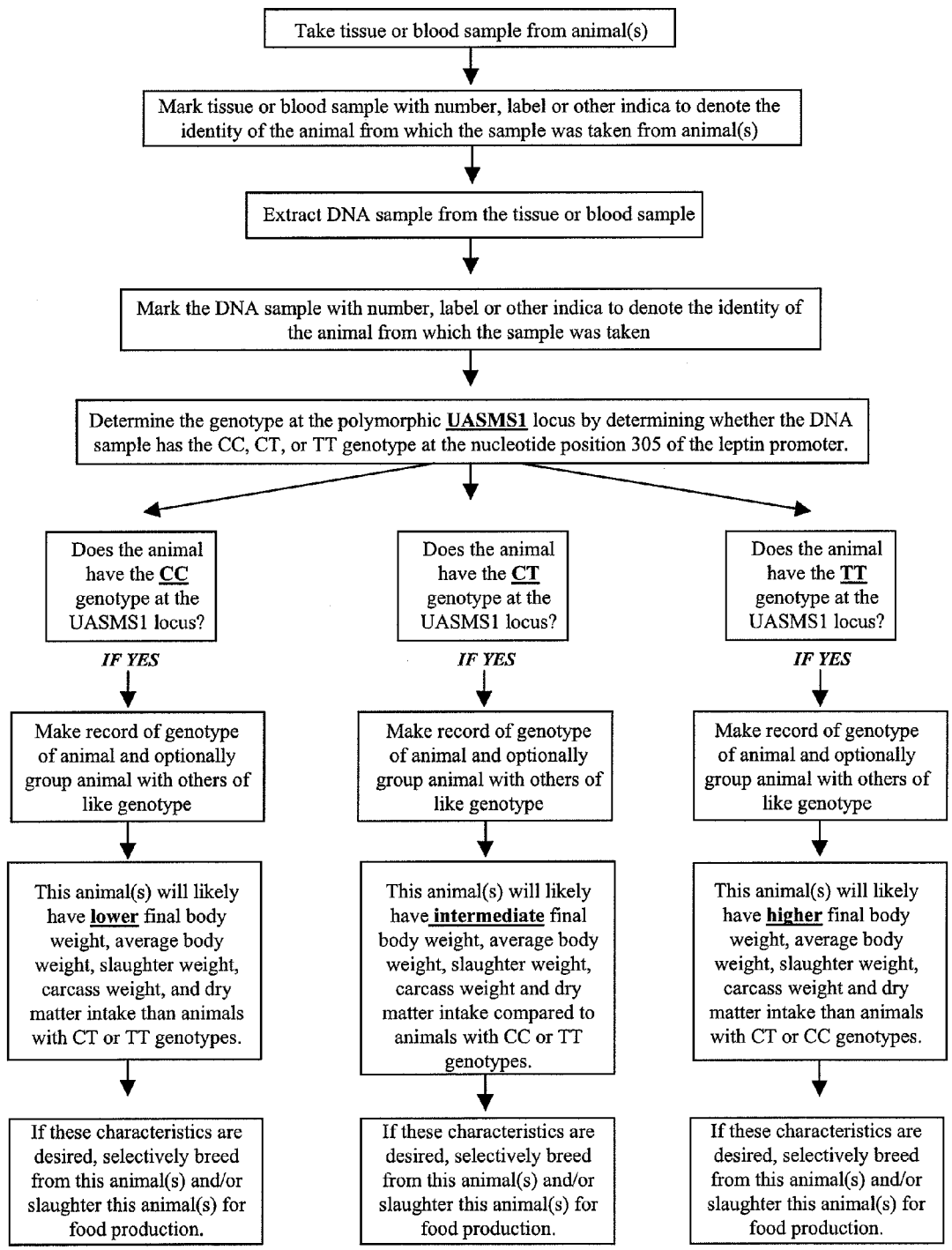
FIG. 7 illustrates using a flow chart how the animals may be screened for the UASMS1 SNP, and how the genotype information may be used to select animals to breed from and/or use for food production.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "animal" is used herein to include all vertebrate animals, including humans. It also includes an individual animal in all stages of development, including embryonic and fetal stages. As used herein, the term "production animals" is used interchangeably with "livestock animals" and refers generally to animals raised primarily for food. For example, such animals include, but are not limited to, cattle (bovine), sheep (ovine), pigs (porcine or swine), poultry (avian), and the like. As used herein, the term "cow" or "cattle" is used generally to refer to an animal of bovine origin of any age. Interchangeable terms include "bovine", "calf", "steer", "bull", "heifer", "cow" and the like. As used herein, the term "pig" is used generally to refer to an animal of porcine origin of any age. Interchangeable terms include "piglet", "sow" and the like.

By the term "complementarity" or "complementary" is meant, for the purposes of the specification or claims, a sufficient number in the oligonucleotide of complementary base pairs in its sequence to interact specifically (hybridize) with the target nucleic acid sequence of the ob gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

A "detectable amount of product" refers to an amount of amplified nucleic acid that can be detected using standard laboratory tools. A "detectable marker" refers to a nucleotide analog that allows detection using visual or other means. For example, fluorescently labeled nucleotides can be incorporated into a nucleic acid during one or more steps of a cyclic polymerase-mediated reaction, thereby allowing the detection of the product of the reaction using, e.g. fluorescence microscopy or other fluorescence-detection instrumentation.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified ob gene polymorphisms sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

By "detectably labeled" is meant that a fragment or an oligonucleotide contains a nucleotide that is radioactive, or that is substituted with a fluorophore, or that is substituted with some other molecular species that elicits a physical or chemical response that can be observed or detected by the naked eye or by means of instrumentation such as, without limitation, scintillation counters, calorimeters, UV spectrophotometers and the like. As used herein, a "label" or "tag" refers to a molecule that, when appended by, for example, without limitation, covalent bonding or hybridization, to another molecule, for example, also without limitation, a polynucleotide or polynucleotide fragment, provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence, electrochemiluminescence, raman, calorimetric, hybridization protection assay, and mass spectrometry.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

"DNA" refers to the polymeric form of deoxyribonucleotides (adenine, guanine, thymine, or cytosine) in either single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). For example, it is known that the protein leptin is encoded by the ob (obese) gene and appears to be involved in the regulation of appetite, basal metabolism and fat deposition. In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

By "immobilized on a solid support" is meant that a fragment, primer or oligonucleotide is attached to a substance at a particular location in such a manner that the system containing the immobilized fragment, primer or oligonucleotide may be subjected to washing or other physical or chemical manipulation without being dislodged from that location. A number of solid supports and means of immobilizing nucleotide-containing molecules to them are known in the art; any of these supports and means may be used in the methods of this invention.

As used herein, the term "increased weight gain" means a biologically significant increase in weight gain above the mean of a given population.

As used herein, the term "locus" or "loci" refers to the site of a gene on a chromosome. A single allele from each locus is inherited from each parent. Each animal's particular combination of alleles is referred to as its "genotype". Where both alleles are identical, the individual is said to be homozygous for the trait controlled by that pair of alleles; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. An "isolated" nucleic acid molecule is one that is separated from other nucleic acid molecules that are present in the natural source of the nucleic acid. A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

"Polymerase chain reaction" or "PCR" refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

A "polymerase" is an enzyme that catalyzes the sequential addition of monomeric units to a polymeric chain, or links two or more monomeric units to initiate a polymeric chain. In advantageous embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides liked by a phosphodiester backbone. A "modified polynucleotide" refers to a polynucleotide in which one or more natural nucleotides have been partially or substantially replaced with modified nucleotides.

A "primer" is an oligonucleotide, the sequence of at least a portion of which is complementary to a segment of a template DNA which to be amplified or replicated. Typically primers are used in performing the polymerase chain reaction (PCR). A primer hybridizes with (or "anneals" to) the template DNA and is used by the polymerase enzyme as the starting point for the replication/amplification process. By "complementary" is meant that the nucleotide sequence of a primer is such that the primer can form a stable hydrogen bond complex with the template; i.e., the primer can hybridize or anneal to the template by virtue of the formation of base-pairs over a length of at least ten consecutive base pairs.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety. Various labeling moieties are known in the art. Said moiety may, for example, either be a radioactive compound, a detectable enzyme (e.g. horse radish peroxidase (HRP)) or any other moiety capable of generating a detectable signal such as a calorimetric, fluorescent, chemiluminescent or electrochemiluminescent signal. The detectable moiety may be detected using known methods.

As used herein, the term "protein" refers to a large molecule composed of one or more chains of amino acids in a specific order. The order is determined by the base sequence of nucleotides in the gene coding for the protein. Proteins are required for the structure, function, and regulation of the body's cells, tissues, and organs. Each protein has a unique function.

As used herein, the terms "quality traits," "traits," or "physical characteristics" refer to advantageous properties of the animal resulting from genetics. Quality traits include, but are not limited to, the animal's genetic ability to metabolize energy, produce milk, put on intramuscular fat, lay eggs, produce offspring, produce particular proteins in meat or milk, or retain protein in milk. Physical characteristics include marbled or lean meats. The terms are used interchangeably.

A "restriction enzyme" refers to an endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to polynucleotide that differs from another polynucleotide by a single nucleotide exchange. For example, without limitation, exchanging one A for one C, G, or T in the entire sequence of polynucleotide constitutes a SNP. Of course, it is possible to have more than one SNP in a particular polynucleotide. For example, at one locus in a polynucleotide, a C may be exchanged for a T, at another locus a G may be exchanged for an A, and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

ii. General Aspects of the Invention

The present invention provides methods for the identification and selection of animals based on the presence of SNPs in the ob (obese) gene—a gene that encodes the protein leptin. Leptin is a 16-kDa adipocyte-specific polypeptide involved in the regulation of appetite, basal metabolism, fat deposition and milk production. The ob gene has been mapped to specific chromosomes in several different animals, allowing the gene to be sequenced in several different species. It has been found that there is significant conservation of ob DNAs and leptin polypeptides between species. SNPs having the same or similar phenotypic effects to those of the present invention may occur in many different animal species The methods of the present invention can be used to determine whether an individual animal from a species of interest possesses the SNPs described herein. In a preferred embodiment, the ob gene of a bovine animal is screened for the presence of the SNPs of the present invention.

In one aspect, the present invention relates to the identification of single nucleotide polymorphisms (SNPs) in the leptin promoter, and to methods for the identification of animals carrying specific alleles of these SNPs that are associated with circulating leptin levels, feed intake, growth rate, body weight, carcass merit and composition, and milk yield. In a further aspect, the present invention relates the association of a previously reported SNP in exon 2 of the leptin gene, with circulating leptin levels, feed intake, growth rate, body weight, carcass merit and composition, and milk yield. The present invention also provides oligonucleotides that can be used as primers to amplify specific nucleic acid sequences of the ob gene, and oligonucleotides that can be used as probes in the detection of nucleic acid sequences of the ob gene.

FIG. 1 illustrates the nucleotide sequence for the 5' flanking promoter region and exon 1 of the "wild type" bovine ob gene. This "wild type" sequence has GenBank accession number AB070368, and is designated herein as SEQ ID NO. 1.

In the present invention it has surprisingly been shown that three previously unknown SNPs (namely UASMS1, UASMS2 and UASMS3) located in the promoter region of the ob gene, and one previously known SNP in exon 2 of the gene are associated with certain economically valuable traits in animals, in particular in bovine livestock.

The SNP termed UASMS1 constitutes a cytosine (C) to thymine (T) substitution (C/T) at position 207 of the bovine leptin gene promoter. The SNP termed UASMS2, constitutes a cytosine (C) to thymine (T) substitution (C/T substitution) at position 528 of bovine leptin gene promoter. The SNP termed UASMS3 constitutes a cytosine (C) to guanine (G) substitution (C/G substitution) at position 1759 of the bovine leptin gene promoter. The nucleotide numbering system used herein for the identification of the leptin promoter SNPs UASMS1, UASMS2 and UASMS3 is that used for the "wild type" bovine leptin promoter sequence SEQ ID NO. 1.

The UASMS1, UASMS2 and UASMS3 polymorphisms are located in the 5' regulatory sequence of the leptin gene, not the coding region of the gene, and thus do not result in any amino acid substitution in the leptin gene product.

The SNP termed EXON2-FB described herein was identified previously by Buchanan et al. (2002), and constitutes a cytosine (C) to thymine (T) missense mutation at position 1759 in exon 2 of the coding region of the "wild type" bovine leptin gene (GenBank accession No. AY138588, and SEQ ID NO. 5). The nucleotide numbering system used herein for the identification of the EXON2-FB SNP is that used for the "wild type" bovine leptin exon 2 sequence SEQ ID NO. 5.

iii. Tissue and DNA Samples

In order to determine the genotype of a given animal according to the methods of the present invention, it is necessary to obtain a sample of genomic DNA from that animal. Typically, that sample of genomic DNA will be obtained from a sample of tissue or cells taken from that animal.

A tissue or cell sample may be taken from an animal at any time in the lifetime of an animal but before the carcass identity is lost. The tissue sample can comprise hair (including roots), hide, bone, buccal swabs, blood, saliva, milk, semen, embryos, muscle or any internal organs. In the method of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art. Ideally, the size/volume of the tissue sample retrieved should be as consistent as possible within the type of sample and the species of animal. For example, for cattle, non-limiting examples of sample sizes/methods include non-fatty meat: 0.0002 g to 0.0010 g; hide: 0.0004 g to 0.0010 g; hair roots: greater than five and less than twenty; buccal swabs: 15 to 20 seconds of rubbing with modest pressure in the area between outer lip and gum using one Cytosoft® cytology brush; bone: 0.0020 g to 0.0040 g; and blood: 30 to 70 µL.

Generally, the tissue sample is placed in a container that is labeled using a numbering system bearing a code corresponding to the animal, for example, to the animal's ear tag. Accordingly, the genotype of a particular animal is easily traceable at all times.

In one embodiment of the invention, a sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

According to the present invention, a sample of genomic DNA is obtained from the tissue sample of the livestock animal of interest. Whatever source of cells or tissue is used, a sufficient amount of cells must be obtained to provide a sufficient amount of DNA for analysis. This amount will be known or readily determinable by those skilled in the art.

DNA is isolated from the tissue/cells by techniques known to those skilled in the art (see, e.g., U.S. Pat. Nos. 6,548,256 and 5,989,431, Hirota et al., Jinrui Idengaku Zasshi. 1989 September; 34(3):217-23 and John et al., Nucleic Acids Res. 1991 Jan. 25; 19(2):408; the disclosures of which are incorporated by reference in their entireties). For example, high molecular weight DNA may be purified from cells or tissue using proteinase K extraction and ethanol precipitation. DNA may be extracted from an animal specimen using any other suitable methods known in the art.

iv. Determining the Genotype of an Animal of Interest

It is an object of the present invention to determine the genotype of a given animal of interest, in order to identify animals carrying specific alleles of the SNPs of the invention that are associated with circulating leptin levels, feed intake, growth rate, body weight, carcass merit and composition, and milk yield.

There are many methods known in the art for determining the genotype of an animal and for identifying whether a given DNA sample contains a particular SNP. Any method for determining genotype can be used for determining the ob genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468, 742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties.

v. Determining the Genotype by Sequencing

In one embodiment, the presence or absence of the SNPs of the present invention is determined by sequencing the region of the genomic DNA sample that spans the polymorphic locus. Many methods of sequencing genomic DNA are known in the art, and any such method can be used, see for example Sambrook et al., Molecular Cloning; A Laboratory Manual 2d ed. (1989). For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, Genome Res. 2000 September; 10(9):1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, Methods Mol Biol. 2001; 167:153-70 and MacBeath et al., Methods Mol Biol. 2001; 167:119-52), capillary electrophoresis (see, e.g., Bosserhoff et al., Comb Chem High Throughput Screen. 2000 December; 3(6):455-66), DNA sequencing chips (see, e.g., Jain, Pharmacogenomics. 2000 August; 1(3):289-307), mass spectrometry (see, e.g., Yates, Trends Genet. 2000 January; 16(1):5-8), pyrosequencing (see, e.g., Ronaghi, Genome Res. 2001 January; 11(1):3-11), and ultrathin-layer gel electrophoresis (see, e.g., Guttman & Ronai, Electrophoresis. 2000 December; 21(18):3952-64), the disclosures of which are hereby incorporated by reference in their entireties. The sequencing can also be done by any commercial company. Examples of such companies include, but are not limited to, the University of Georgia Molecular Genetics Instrumentation Facility (Athens, Ga.) or Seq Wright DNA Technologies Services (Houston, Tex.).

vi) Determining the Genotype Using Cyclic Polymerase Mediated Amplification

In certain embodiments of the present invention, the detection of a given SNP can be performed using cyclic polymerase-mediated amplification methods. Any one of the methods known in the art for amplification of DNA may be used, such as for example, the polymerase chain reaction (PCR), the ligase chain reaction (LCR) (Barany, F., Proc. Natl. Acad. Sci. (U.S.A.) 88:189-193 (1991)), the strand displacement assay (SDA), or the oligonucleotide ligation assay ("OLA") (Landegren, U. et al., Science 241:1077-1080

(1988)). Nickerson, D. A. et al. have described a nucleic acid detection assay that combines attributes of PCR and OLA (Nickerson, D. A. et al., Proc. Natl. Acad. Sci. (U.S.A.) 87: 8923-8927 (1990)). Other known nucleic acid amplification procedures, such as transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT Application WO89/06700; Kwoh, D. et al., Proc. Natl. Acad. Sci. (U.S.A.) 86:1173 (1989); Gingeras, T. R. et al., PCT Application WO88/10315)), or isothermal amplification methods (Walker, G. T. et al., Proc. Natl. Acad. Sci. (U.S.A.) 89:392-396 (1992)) may also be used.

The most advantageous method of amplifying DNA fragments containing the SNPs of the invention employs PCR (see e.g., U.S. Pat. Nos. 4,965,188; 5,066,584; 5,338,671; 5,348,853; 5,364,790; 5,374,553; 5,403,707; 5,405,774; 5,418,149; 5,451,512; 5,470,724; 5,487,993; 5,523,225; 5,527,510; 5,567,583; 5,567,809; 5,587,287; 5,597,910; 5,602,011; 5,622,820; 5,658,764; 5,674,679; 5,674,738; 5,681,741; 5,702,901; 5,710,381; 5,733,751; 5,741,640; 5,741,676; 5,753,467; 5,756,285; 5,776,686; 5,811,295; 5,817,797; 5,827,657; 5,869,249; 5,935,522; 6,001,645; 6,015,534; 6,015,666; 6,033,854; 6,043,028; 6,077,664; 6,090,553; 6,168,918; 6,174,668; 6,174,670; 6,200,747; 6,225,093; 6,232,079; 6,261,431; 6,287,769; 6,306,593; 6,440,668; 6,468,743; 6,485,909; 6,511,805; 6,544,782; 6,566,067; 6,569,627; 6,613,560; 6,613,560 and 6,632,645; the disclosures of which are incorporated by reference in their entireties), using primer pairs that are capable of hybridizing to the proximal sequences that define or flank a polymorphic site in its double-stranded form.

To perform a cyclic polymerase mediated amplification reaction according to the present invention, the primers are hybridized or annealed to opposite strands of the target DNA, the temperature is then raised to permit the thermostable DNA polymerase to extend the primers and thus replicate the specific segment of DNA spanning the region between the two primers. Then the reaction is thermocycled so that at each cycle the amount of DNA representing the sequences between the two primers is doubled, and specific amplification of the ob gene DNA sequences, if present, results.

Any of a variety of polymerases can be used in the present invention. For thermocyclic reactions, the polymerases are thermostable polymerases such as Taq, KlenTaq, Stoffel Fragment, Deep Vent, Tth, Pfu, Vent, and UlTma, each of which are readily available from commercial sources. For non-thermocyclic reactions, and in certain thermocyclic reactions, the polymerase will often be one of many polymerases commonly used in the field, and commercially available, such as DNA pol 1, Klenow fragment, T7 DNA polymerase, and T4 DNA polymerase. Guidance for the use of such polymerases can readily be found in product literature and in general molecular biology guides.

Typically, the annealing of the primers to the target DNA sequence is carried out for about 2 minutes at about 37-55° C., extension of the primer sequence by the polymerase enzyme (such as Taq polymerase) in the presence of nucleoside triphosphates is carried out for about 3 minutes at about 70-75° C., and the denaturing step to release the extended primer is carried out for about 1 minute at about 90-95° C. However, these parameters can be varied, and one of skill in the art would readily know how to adjust the temperature and time parameters of the reaction to achieve the desired results. For example, cycles may be as short as 10, 8, 6, 5, 4.5, 4, 2, 1, 0.5 minutes or less.

Also, "two temperature" techniques can be used where the annealing and extension steps may both be carried out at the same temperature, typically between about 60-65° C., thus reducing the length of each amplification cycle and resulting in a shorter assay time.

Typically, the reactions described herein are repeated until a detectable amount of product is generated. Often, such detectable amounts of product are between about 10 ng and about 100 ng, although larger quantities, e.g. 200 ng, 500 ng, 1 mg or more can also, of course, be detected. In terms of concentration, the amount of detectable product can be from about 0.01 pmol, 0.1 pmol, 1 pmol, 10 pmol, or more. Thus, the number of cycles of the reaction that are performed can be varied, the more cycles are performed, the more amplified product is produced. In certain embodiments, the reaction comprises 2, 5, 10, 15, 20, 30, 40, 50, or more cycles.

For example, the PCR reaction may be carried out using about 25-50 µl samples containing about 0.01 to 1.0 ng of template amplification sequence, about 10 to 100 pmol of each generic primer, about 1.5 units of Taq DNA polymerase (Promega Corp.), about 0.2 mM dDATP, about 0.2 mM dCTP, about 0.2 mM dGTP, about 0.2 mM dTTP, about 15 mM $MgCl_2$, about 10 mM Tris-HCl (pH 9.0), about 50 mM KCl, about 1 µg/ml gelatin, and about 10 µl/ml Triton X-100 (Saiki, 1988).

Those of skill in the art are aware of the variety of nucleotides available for use in the cyclic polymerase mediated reactions. Typically, the nucleotides will consist at least in part of deoxynucleotide triphosphates (dNTPs), which are readily commercially available. Parameters for optimal use of dNTPs are also known to those of skill, and are described in the literature. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as chain-terminating nucleotides, dideoxynucleotides and boronated nuclease-resistant nucleotides. Commercial kits containing the reagents most typically used for these methods of DNA sequencing are available and widely used. Other nucleotide analogs include nucleotides with bromo-, iodo-, or other modifying groups, which affect numerous properties of resulting nucleic acids including their antigenicity, their replicatability, their melting temperatures, their binding properties, etc. In addition, certain nucleotides include reactive side groups, such as sulfhydryl groups, amino groups, N-hydroxysuccinimidyl groups, that allow the further modification of nucleic acids comprising them.

The present invention provides oligonucleotides that can be used as primers to amplify specific nucleic acid sequences of the ob gene in cyclic polymerase-mediated amplification reactions, such as PCR reactions. These primers are useful in detecting the UASMS1, UASMS2 or UASMS3 SNPs in the leptin promoter, and the exon2-FB SNP in exon 2 of the leptin gene. In certain embodiments, these primers consist of oligonucleotide fragments. Such fragments should be of sufficient length to enable specific annealing or hybridization to the nucleic acid sample. The sequences typically will be about 8 to about 44 nucleotides in length, but may be longer. Longer sequences, e.g., from about 14 to about 50, are advantageous for certain embodiments.

In embodiments where it is desired to amplify a fragment of DNA comprising the UASMS1, UASMS2 or UASMS3 SNPs, primers having contiguous stretches of about 8, 9, 10, 11, 12, 13, 14, 15, 16, 17, 18, 19, 20, 21, 22, 23, or 24 nucleotides from SEQ ID NO: 1 (the leptin promoter sequence) are contemplated. In embodiments where it is desired to amplify a fragment of DNA comprising the EXON2-FB SNP, primers having contiguous stretches of about 8, 9, 10, 11, 12, 13, 14, 15, 16, 17, 18, 19, 20, 21, 22, 23, or 24 nucleotides from SEQ ID NO: 5 (exon 2 of the leptin gene) are contemplated.

Although various different lengths of primers can be used, and the exact location of the stretch of contiguous nucleotides in leptin gene used to make the primer can vary, it is important that the sequences to which the forward and reverse primers anneal are located on either side of the particular nucleotide position that is substituted in the SNP to be amplified. For example, when designing primers for amplification of the UASMS1 polymorphism, one primer must be located upstream of (not overlapping with) nucleotide position 207 of the leptin promoter (SEQ ID NO: 1, or 2), and the other primer must be located downstream of (not overlapping with) nucleotide position 207 of the leptin promoter (SEQ ID NO: 1, or 2). When designing primers for amplification of the UASMS2 polymorphism, one primer must be located upstream of (not overlapping with) nucleotide position 528 of the leptin promoter (SEQ ID NO: 1, or 3), and the other primer must be located downstream of (not overlapping with) nucleotide position 528 of the leptin promoter (SEQ ID NO: 1, or 3). Similarly, when designing primers for amplification of the UASMS3 polymorphism one primer must be located upstream of (not overlapping with) nucleotide position 1759 of the leptin promoter (SEQ ID NO: 1, or 4), and the other primer must be located downstream of (not overlapping with) nucleotide position 1759. Finally, when designing primers for amplification of the EXON2-FB polymorphism one primer must be located upstream of (not overlapping with) nucleotide position 305 of exon 2 (SEQ ID NO: 5), and the other primer must be located downstream of (not overlapping with) nucleotide position 305 of exon 2.

In a preferred embodiment, a fragment of DNA spanning and containing the location of the UASMS1 polymorphism is amplified from a nucleic acid sample using a forward primer having the sequence 5'-GGCACAATCCTGTGTATTGG-TAAGA-3' (SEQ ID NO: 7), and a reverse primer having the sequence 5'-GTCCATGTACCATTGCCCAATTT-3' (SEQ ID NO: 8).

Similarly, in a preferred embodiment, a fragment of DNA spanning the location of the UASMS2 polymorphism is amplified from a nucleic acid sample using a forward primer having the sequence 5'-AGGTGCCCAGGGACTCA-3'(SEQ ID NO: 11), and a reverse primer having the sequence 5'-CAACAAAGGCCGTGTGACA-3' (SEQ ID NO: 12).

For amplification of a fragment of DNA spanning the location of the UASMS3 polymorphism, it is preferred that a forward primer having the sequence 5'-ATGTATATTTTG-GTGTGAGAGTGTGTGT-3' (SEQ. I.D. NO.: 15), and a reverse primer having the sequence 5'-AGCTGGAAA-GAACGGATTATAAAATGGT-3' (SEQ. I.D. NO.: 16), is used.

Likewise, for amplification of a fragment of DNA spanning the location of the EXON2-FB polymorphism, it is preferred that a forward primer having the sequence 5'-GGCTTTGGC-CCTATCTGTCTTAC-3' (SEQ ID NO: 19), and a reverse primer having the sequence 5'-CTTGATGAGGGTTTTG-GTGTCA-3' (SEQ ID NO: 20), is used.

The above methods employ primers located on either side of, and not overlapping with, the SNP in order to amplify a fragment of DNA that includes the nucleotide position at which the SNP is located. Such methods require additional steps, such as sequencing of the fragment, or hybridization of allele specific probes to the fragment, in order to determine the genotype at the polymorphic site. However, in some embodiments of the present invention, the amplification method is itself a method for determining the genotype of the polymorphic site, as for example, in "allele-specific PCR". In allele-specific PCR, primer pairs are chosen such that amplification itself is dependent upon the input template nucleic acid containing the polymorphism of interest. In such embodiments, primer pairs are chosen such that at least one primer spans the actual nucleotide position of the SNP and is therefore an allele-specific oligonucleotide primer. Typically, the primers contain a single allele-specific nucleotide at the 3' terminus preceded by bases that are complementary to the gene of interest. The PCR reaction conditions are adjusted such that amplification by a DNA polymerase proceeds from matched 3'-primer termini, but does not proceed where a mismatch occurs. Allele specific PCR can be performed in the presence of two different allele-specific primers, one specific for each allele, where each primer is labeled with a different dye, for example one allele specific primer may be labeled with a green dye (e.g. fluorescein) and the other allele specific primer labeled with a red dye (e.g. sulforhodamine). Following amplification, the products are analyzed for green and red fluorescence. The aim is for one homozygous genotype to yield green fluorescence only, the other homozygous genotype to give red fluorescence only, and the heterozygous genotype to give mixed red and green fluorescence.

Thus, to perform allele specific PCR to detect the UASMS1 polymorphism, one primer must overlap nucleotide position 207 of SEQ ID NO: 1 or SEQ ID NO: 2 such that nucleotide position 207 is at the 3' terminus of the primer. Similarly, to perform allele specific PCR to detect the UASMS2 polymorphism, one primer must overlap nucleotide position 528 of SEQ ID NO: 1 or SEQ ID NO: 3 such that nucleotide position 528 is at the 3' terminus of the primer. To perform allele specific PCR to detect the UASMS3 polymorphism, one primer must overlap nucleotide position 1759 of SEQ ID NO: 1 or SEQ ID NO: 4 such that nucleotide position 1759 is at the 3' terminus of the primer. Finally, when designing allele specific primers for detection of the EXON2-FB polymorphism, one primer must overlap nucleotide position 305 of SEQ ID NO: 5 or SEQ ID NO: 6 such that nucleotide position 305 is at the 3' terminus of the primer.

Methods for performing allele specific PCR are well known in the art, and any such methods may be used. For example suitable methods are taught in Myakishev et al. Genome Research, vol 1, p 163-169 (2001), Alexander et al. Mol Biotechnol. vol 28(3), p 171-174 (2004), and Ruano et al. Nucleic Acids Res. vol 17(20), p 8392 (1989), the contents of which are incorporated by reference. In some embodiments of the present invention, allele-specific primers are chosen so that amplification creates a restriction site, facilitating identification of a polymorphic site. To perform, allele specific PCR the reaction conditions must be carefully adjusted such that the allele specific primer will only bind to one allele and not the alternative allele, for example, in some embodiments the conditions are adjusted so that the primers will only bind where there is a 100% match between the primer sequence and the DNA, and will not bind if there is a single nucleotide mismatch.

vii) Determining the Genotype Using Hybridization-Based Methods

In certain embodiments of the present invention, the detection of a given SNP can be performed using oligonucleotide probes that bind or hybridize to the DNA. The present invention provides oligonucleotide probes to detect the UASMS1, UASMS2 or UASMS3 SNPs in the bovine leptin promoter, or the EXON2-FB SNP in exon 2 of the bovine leptin gene.

In certain embodiments, these probes consist of oligonucleotide fragments. Such fragments should be of sufficient length to provide specific hybridization to the nucleic acid sample. The sequences typically will be about 8 to about 50 nucleotides, but may be longer. Nucleic acid probes having contiguous stretches of about 8, 9, 10, 11, 12, 13, 14, 15, 16, 17, 18, 19, 20, 21, 22, 23, or 24 nucleotides from a sequence selected from SEQ ID NO: 1 (wild-type bovine leptin promoter), SEQ ID NO:2 (bovine leptin promoter with UASMS1 polymorphism), SEQ ID NO:3 (bovine leptin promoter with UASMS2 polymorphism), SEQ ID NO:4 (bovine leptin promoter with UASMS3 polymorphism), SEQ ID NO:5 (wild-type bovine leptin exon 2) or SEQ ID NO:6 (leptin exon 2 with EXON2-FB polymorphism) are contemplated.

Although various different lengths of probes can be used, and the precise location of the stretch of contiguous nucleotides in the leptin gene from which the probe sequence is derived can vary, the probe sequence must span the particular nucleotide position that is substituted in the particular SNP to be detected. For example, probes designed for detection of the bovine UASMS1 polymorphism must span nucleotide position 207 of the bovine leptin promoter (SEQ ID NO: 2). Probes designed for detection of the bovine UASMS2 polymorphism must span nucleotide position 528 of the bovine leptin promoter (SEQ ID NO: 3). Similarly, probes designed for detection of the bovine UASMS3 polymorphism must span nucleotide position 1759 of the bovine leptin promoter (SEQ ID NO: 4). Finally, probes designed for detection of the bovine exon2-FB polymorphism must span nucleotide position 305 of exon 2 of the bovine leptin gene (SEQ ID NO: 6).

These probes will be useful in a variety of hybridization embodiments, such as Southern blotting, Northern blotting, and hybridization disruption analysis. Also the probes of the invention can be used to detect SNPs in amplified sequences, such as amplified PCR products generated using the primers described above. For example, in one embodiment a target nucleic acid is first amplified, such as by PCR or strand displacement amplification (SDA), and the amplified double stranded DNA product is then denatured and hybridized with a probe.

In other embodiments double stranded DNA (amplified or not) is denatured and hybridized with a probe of the present invention and then the hybridization complex is subjected to destabilizing or disrupting conditions. By determining the level of disruption energy required wherein the probe has different disruption energy for one allele as compared to another allele, the genotype of a gene at a polymorphic locus can be determined. In one example, there can be lower disruption energy, e.g., melting temperature, for an allele that harbors a cytosine residue at a polymorphic locus, and a higher required energy for an allele with a thymine residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In one embodiment the destabilizing conditions comprise an elevation of temperature. The higher the temperature, the greater the degree of destabilization. In another embodiment, the destabilizing conditions comprise subjecting the hybridization complex to a temperature gradient, whereby, as the temperature is increased, the degree of destabilization increases. In an alternative embodiment, the destabilizing conditions comprise treatment with a destabilizing compound, or a gradient comprising increasing amounts of such a compound. Suitable destabilizing compounds include, but are not limited to, salts and urea. Methods of destabilizing or denaturing hybridization complexes are well known in the art, and any such method may be used in accordance with the present invention. For example, methods of destabilizing or denaturing hybridization complexes are taught by Sambrook et al., Molecular Cloning; A Laboratory Manual 2d ed. (1989).

For optimal detection of single-base pair mismatches, it is preferable that there is about a 1° C. to about a 10° C. difference in melting temperature of the probe DNA complex when bound to one allele as opposed to the alternative allele at the polymorphic site. Thus, when the temperature is raised above the melting temperature of a probe: DNA duplex corresponding to one of the alleles, that probe will disassociate.

In one embodiment of the above method, a second ("anchor") probe can be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe, for example for use in fluorescence resonance energy transfer or "FRET." A sensor probe acquires energy from the anchor probe once conditions are adequate for hybridization between the target DNA and the anchor and sensor probes. Once hybridization occurs, the anchor probe transfers its florescence energy to the sensor probe, which only will emit a specific wavelength after it has acquired the energy from the anchor probe. Detection of the SNP occurs as the temperature is raised at a predetermined rate, and a reading is acquired from the florescent light emitted. If there is a single base mismatch of the probe and target DNA caused by the presence of the alternative polymorphic nucleotide (i.e. the SNP) the sensor probe will dissociate sooner, or at a lower temperature, since the homology between the genomic DNA and the sensor probe will be less than that of genomic DNA that does not harbor the altered nucleotide or SNP. Thus, there will be a loss of fluorescence that can be detected. Where the probe is designed to bind to the wild-type sequence, the dissociation of the probe from the DNA (i.e. the "melting") will occur at a lower temperature if the SNP is present, since the stability of the binding of the probe to the SNP is slightly less than for the wild-type sequence. This occurs, obviously, on both chromosomes at the same time, thus yielding either a reading of two identical melting temperatures for a homozygote, or a reading of two different melting temperatures for the heterozygote. For example, where a probe is designed to have the sequence of the C-containing allele of the UASMS1 polymorphism, the probe will dissociate or melt at a lower temperature in DNA samples from individuals that harbor two copies of the polymorphic T-containing allele, than in individuals that harbor two copies of the C-containing allele.

In other embodiments, two different "allele-specific probes" can be used for analysis of a SNP, a first allele-specific probe for detection of one allele, and a second allele-specific probe for the detection of the alternative allele. For example, in one embodiment the different alleles of the UASMS1 ob polymorphism can be detected using two different allele-specific probes, one for detecting the T-containing allele at nucleotide position 207 of the ob gene promoter, and another for detecting the C-containing allele at nucleotide position 207 of the ob gene promoter. In a preferred embodiment an oligonucleotide probe having the sequence of 5'-CTTTCACCTAGTATATCTAG-3' (SEQ ID NO: 9) is used to detect the T-containing allele, and an oligonucleotide probe having the sequence of 5'-TCTTTCACCTAGTAT GTCTAG-3' (SEQ ID NO: 10) is used to detect the C-containing allele.

In another embodiment the different alleles of the UASMS2 ob polymorphism can be detected using two different allele-specific probes, one for detecting the T-containing allele at nucleotide position 528 of the ob gene promoter, and another for detecting the C-containing allele at nucleotide position 528 of the ob gene promoter. In a preferred embodiment an oligonucleotide probe having the sequence of 5'-AAGCTCTAGAGCCTATGT-3' (SEQ ID NO: 13) is used to detect the T-containing allele, and an oligonucleotide probe having the sequence of 5'-CAAGCTCTAGAGCCTGTGT-3' (SEQ ID NO: 14) is used to detect the C-containing allele.

In another embodiment the different alleles of the UASMS3 ob polymorphism can be detected using two different allele-specific probes, one for detecting the G-containing allele at nucleotide position 1759 of the ob gene promoter, and another for detecting the C-containing allele at nucleotide position 1759 of the ob gene promoter. In a preferred embodiment an oligonucleotide probe having the sequence of 5'-CACACATTCCAATCAA-3' (SEQ ID NO: 17) is used to detect the G-containing allele, and an oligonucleotide probe having the sequence of 5'-CACATTGCAATCAA-3' (SEQ ID NO: 18) is used to detect the C-containing allele.

In a further embodiment the different alleles of the EXON2-FB ob polymorphism can be detected using two different allele-specific probes, one for detecting the T-containing allele at nucleotide position 305 of exon 2 of the ob gene, and another for detecting the C-containing allele at nucleotide position 305 of exon 2 of the ob gene. In a preferred embodiment an oligonucleotide probe having the sequence of 5'-CCTTGCAGATGGG-3' (SEQ ID NO: 21) is used to detect the T-containing allele, and an oligonucleotide probe having the sequence of 5'-CCTTGCGGATGGG-3' (SEQ ID NO: 22) is used to detect the C-containing allele.

Whichever probe sequences and hybridization methods are used, one skilled in the art can readily determine suitable hybridization conditions, such as temperature and chemical conditions. Such hybridization methods are well known in the art. For example, for applications requiring high selectivity, one will typically desire to employ relatively stringent conditions for the hybridization reactions, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and are particularly suitable for detecting specific SNPs according to the present invention. It is generally appreciated that conditions can be rendered more stringent by the addition of increasing amounts of formamide. Other variations in hybridization reaction conditions are well known in the art (see for example, Sambrook et al., Molecular Cloning; A Laboratory Manual 2d ed. (1989)).

viii) Other Suitable Primer and Probe Sequences

In addition to the SNPs described above, it will be appreciated by those skilled in the art that other DNA sequence polymorphisms of the ob gene may exist within a population. Such natural allelic variations can typically result in about 1-5% variance in the nucleotide sequence of the gene. For example, SEQ ID NO 2: provides a sequence of a region of the ob gene promoter containing a polymorphism at nucleotide position 207 (i.e. the UASMS1 SNP). It is possible that other polymorphic loci may also exist within this fragment. In addition to naturally-occurring allelic variants of the nucleotide sequence, the skilled artisan will further appreciate that changes can be introduced by mutation into the nucleotide sequence of the nucleotide sequences described herein. Any and all such additional nucleotide variations are intended to be within the scope of the invention. Thus, for example a probe according to the present invention may be designed to bind to a sequence of the ob gene containing not only the UASMS1 polymorphism, but also other SNPs that may occur within the same region.

Moreover, nucleic acid molecules that differ from the sequences of the primers and probes disclosed herein, are intended to be within the scope of the invention. Nucleic acid sequences that are complementary to these sequences, or that are hybridizable to the sequences described herein under conditions of standard or stringent hybridization, and also analogs and derivatives are also intended to be within the scope of the invention. Advantageously, such variations will differ from the sequences described herein by only a small number of nucleotides, for example by 1, 2, or 3 nucleotides.

Nucleic acid molecules corresponding to natural allelic variants, homologues (i.e., nucleic acids derived from other species), or other related sequences (e.g., paralogs) of the sequences described herein can be isolated based on their homology to the nucleic acids disclosed herein, for example by performing standard or stringent hybridization reactions using all or a portion of the sequences of the invention as probes. Such methods for nucleic acid hybridization and cloning are well known in the art.

Similarly, a nucleic acid molecule of the invention may include only a fragment of the specific sequences described. Fragments provided herein are defined as sequences of at least 6 (contiguous) nucleic acids, a length sufficient to allow for specific hybridization of nucleic acid primers or probes, and are at most some portion less than a full-length sequence. Fragments may be derived from any contiguous portion of a nucleic acid sequence of choice. Derivatives and analogs may be full length or other than full length, if the derivative or analog contains a modified nucleic acid or amino acid, as described below.

Derivatives, analogs, homologues, and variants of the nucleic acids of the invention include, but are not limited to, molecules comprising regions that are substantially homologous to the nucleic acids of the invention, in various embodiments, by at least about 70%, 80%, 85%, 90%, 95%, 96%, 97%, 98%, or even 99% identity (with an advantageous identity of 80-99%) over a nucleic acid sequence of identical size or when compared to an aligned sequence in which the alignment is done by a computer homology program known in the art.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. Without undue experimentation, the skilled artisan can consult with many other programs or references for determining percent homology.

ix) Producing the Primers and Probes of the Invention

The primers and probes described herein may be readily prepared by, for example, directly synthesizing the fragment by chemical means or by introducing selected sequences into recombinant vectors for recombinant production. Methods for making a vector or recombinants or plasmid for amplification of the fragment either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; W091/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312.

x) Labeling and Detecting the Primers and Probes of the Invention

Oligonucleotide sequences used as primers or probes according to the present invention may be labeled with a detectable moiety. As used herein the term "sensors" refers to such primers or probes labeled with a detectable moiety. Various labeling moieties are known in the art. Said moiety may be, for example, a radiolabel (e.g., $^3H$, $^{125}I$, $^{35}S$, $^{14}C$, $^{32}P$, etc.), detectable enzyme (e.g. horse radish peroxidase (HRP), alkaline phosphatase etc.), a fluorescent dye (e.g., fluorescein isothiocyanate, Texas red, rhodamine, Cy3, Cy5, Bodipy, Bodipy Far Red, Lucifer Yellow, Bodipy 630/650-X, Bodipy R6G-X and 5-CR 6G, and the like), a colorimetric label such as colloidal gold or colored glass or plastic (e.g. polystyrene, polypropylene, latex, etc.), beads, or any other moiety capable of generating a detectable signal such as a colorimetric, fluorescent, chemiluminescent or electrochemiluminescent (ECL) signal.

Primers or probes may be labeled directly or indirectly with a detectable moiety, or synthesized to incorporate the detectable moiety. In one embodiment, a detectable label is incorporated into a nucleic acid during at least one cycle of a cyclic polymerase-mediated amplification reaction. For example, polymerases can be used to incorporate fluorescent nucleotides during the course of polymerase-mediated amplification reactions. Alternatively, fluorescent nucleotides may be incorporated during synthesis of nucleic acid primers or probes. To label an oligonucleotide with the fluorescent dye, one of conventionally-known labeling methods can be used (Nature Biotechnology, 14, 303-308, 1996; Applied and Environmental Microbiology, 63, 1143-1147, 1997; Nucleic Acids Research, 24, 4532-4535, 1996). An advantageous probe is one labeled with a fluorescent dye at the 3' or 5' end and containing G or C as the base at the labeled end. If the 5' end is labeled and the 3'end is not labeled, the OH group on the C atom at the 3'-position of the 3' end ribose or deoxyribose may be modified with a phosphate group or the like although no limitation is imposed in this respect.

Spectroscopic, photochemical, biochemical, immunochemical, electrical, optical or chemical means can be used to detect such labels. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. In other embodiments the detection may be via conductivity differences between concordant and discordant sites, by quenching, by fluorescence perturbation analysis, or by electron transport between donor and acceptor molecules.

In yet another embodiment, detection may be via energy transfer between molecules in the hybridization complexes in PCR or hybridization reactions, such as by fluorescence energy transfer (FET) or fluorescence resonance energy transfer (FRET). In FET and FRET methods, one or more nucleic acid probes are labeled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g. on the same, or a neighboring molecule). FET and FRET techniques are well known in the art, and can be readily used to detect the SNPs of the present invention. See for example U.S. Pat. Nos. 5,668, 648, 5,707,804, 5,728,528, 5,853,992, and 5,869,255 (for a description of FRET dyes), Tyagi et al. Nature Biotech. vol. 14, p 303-8 (1996), and Tyagi et al., Nature Biotech. vol 16, p 49-53 (1998) (for a description of molecular beacons for FET), and Mergny et al. Nucleic Acid Res. vol 22, p 920-928, (1994) and Wolf et al. PNAS vol 85, p 8790-94 (1988) (for general descriptions and methods fir FET and FRET), each of which is hereby incorporated by reference.

xi) Compositions and Kits for Detection of the SNPs of the Invention

The oligonucleotide primers and probes of the present invention have commercial applications in diagnostic kits for the detection of the UASMS1, UASMS2, UASMS3 and EXON2-FB ob gene SNPs in livestock specimens. A test kit according to the invention may comprise any of the oligonucleotide primers or probes according to the invention. Such a test kit may additionally comprise one or more reagents for use in cyclic polymerase mediated amplification reactions, such as DNA polymerases, nucleotides (dNTPs), buffers, and the like. An SNP detection kit may also include, a lysing buffer for lysing cells contained in the specimen.

A test kit according to the invention may comprise a pair of oligonucleotide primers according to the invention and a probe comprising an oligonucleotide according to the invention. In some embodiments such a kit will contain two allele specific oligonucleotide probes. Advantageously, the kit further comprises additional means, such as reagents, for detecting or measuring the binding or the primers and probes of the present invention, and also ideally a positive and negative control.

The present invention further encompasses probes according to the present invention that are immobilized on a solid or flexible support, such as paper, nylon or other type of membrane, filter, chip, glass slide, microchips, microbeads, or any other such matrix, all of which are within the scope of this invention. The probe of this form is now called a "DNA chip". These DNA chips can be used for analyzing the SNPs of the present invention. The present invention further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874, 219; 6,114,122; 6,238,910; 6,365,418; 6,410,229; 6,420,114; 6,432,696; 6,475,808 and 6,489,159 and PCT Publication No. WO 01/45843 A2, the disclosures of which are incorporated by reference in their entireties.

xii) Methods of Grouping and Selecting Animals According to SNP Genotype

As described in detail above, the present invention provides reagents and methods for the detection of the UASMS1, UASMS2, UASMS3 and EXON2-FB SNPs in DNA samples obtained from individual animals. For example, using the methods of the present invention, one can determine whether a given animal has a cytosine or a thymine at the polymorphic UASMS1 locus (located at nucleotide position 207 of the ob gene promoter). Having used the methods of the invention to determine the genotype of an animal of interest at either the UASMS1, UASMS2, UASMS3 and/or EXON2-FB a polymorphic loci, it is a further object of the present invention to utilize this genotype information to select and/or group animals according to their genotype.

As described in the Examples, certain alleles of the UASMS1, UASMS2, UASMS3 and EXON2-FB SNPs are associated with certain economically important traits such as circulating leptin levels, feed intake, growth rate, body weight, carcass merit and composition, and milk yield. For example, the present invention demonstrates that the T allele of the UASMS2 locus is significantly associated with serum leptin concentration, being lowest in homozygous animals with the CC genotype, intermediate in heterozygous animals with the CT genotype, and highest in homozygous TT animals. Thus in one embodiment, where it is desirable to group animals according to circulating leptin concentration (for example for use in food production or for breeding), animals can be selected and grouped according to their genotype at the polymorphic UASMS1 locus. Associations between the genotypes of each of the UASMS1, UASMS2, UASMS3 and EXON2-FB polymorphic loci and various other economically important traits are described in the Examples. Thus, for each of these traits, animals can be grouped according to genotype.

Figure 8:
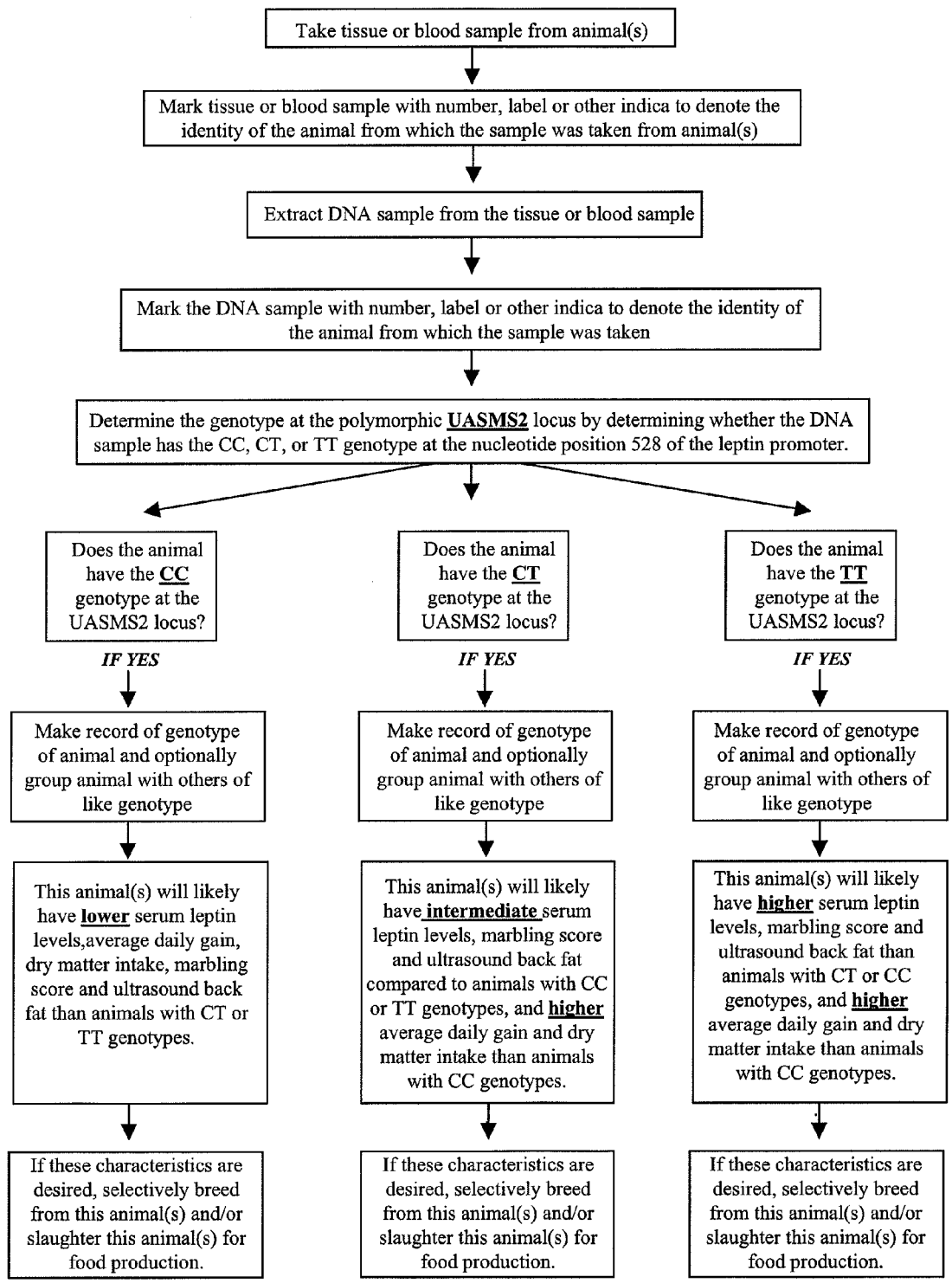
FIG. 8 illustrates using a flow chart how the animals may be screened for the UASMS2 SNP, and how the genotype information may be used to select animals to breed from and/or use for food production.
Figure 9:
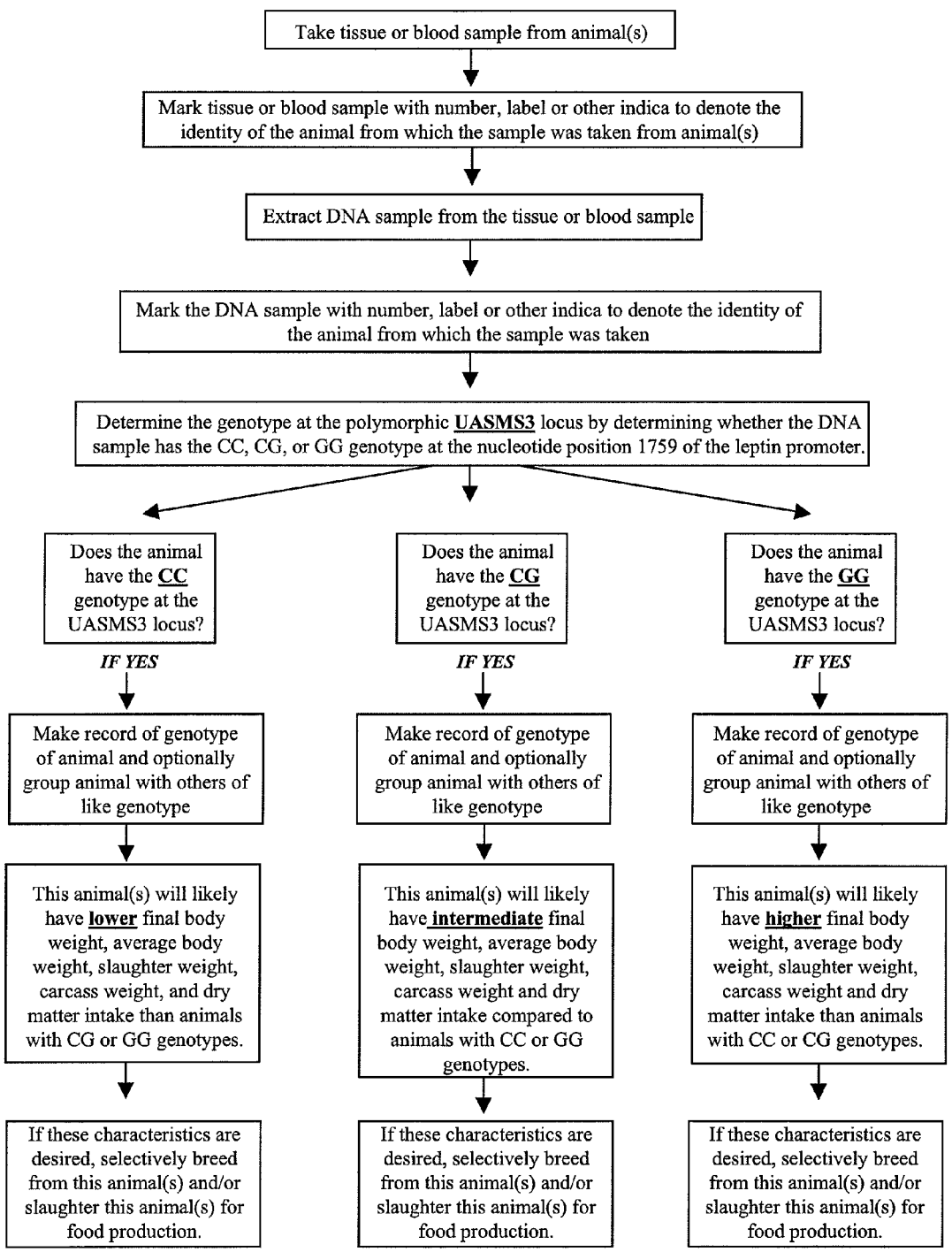
FIG. 9 illustrates using a flow chart how the animals may be screened for the UASMS3 SNP, and how the genotype information may be used to select animals to breed from and/or use for food production.
Figure 10:
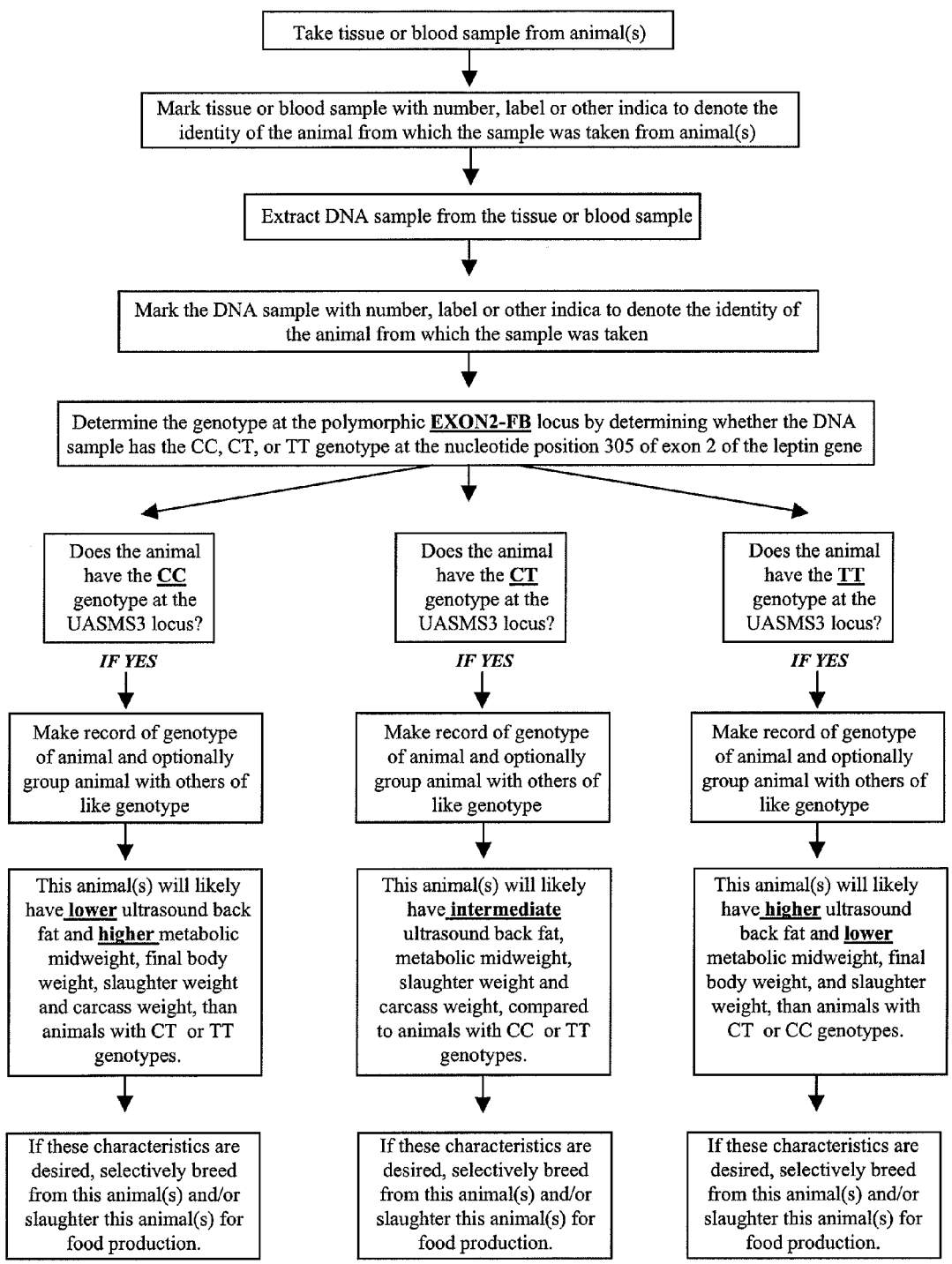
FIG. 10 illustrates using a flow chart how the animals may be screened for the EXON2-FB SNP, and how the genotype information may be used to select animals to breed from and/or use for food production.

FIGS. 7, 8, 9, and 10 illustrate using flow charts how the animals may be screened for the UASMS1, UASMS2, UASMS3, and EXON2-FB SNPs respectively, and illustrate how the genotype information may be used to select animals to breed from and/or use for food production. The methods outlined in these flow charts are not intended to be limiting, and those skilled in the art would recognize that various aspects of these methods could be altered without affecting the overall result. FIG. 7-10 illustrate some of the phenotypic characteristics that are associated with each genotype. Other phenotypes that show some level of correlation to each genotype are shown in the Examples section.

Thus, in one embodiment, the present invention provides methods for grouping animals and methods for managing livestock production comprising grouping livestock animals, such as cattle, according to genotype of the UASMS1, UASMS2, UASMS3 and/or EXON2-FB polymorphic loci. The genetic selection and grouping methods of the present invention can be used in conjunction with other conventional phenotypical grouping methods such as grouping animals by visible characteristics such as weight, frame size, breed traits, and the like.

The methods of the present invention provide for selecting cattle having improved heritable traits, and can be used to optimize the performance of livestock herds in areas such as breeding, food consumption, carcass/meat quality and milk production. The present invention provides methods of screening livestock to determine those more likely to develop a desired body condition by identifying the presence or absence of a polymorphism in the ob genes that is correlated with that body condition.

As described above, and in the Examples, there are various phenotypic traits with which the SNPs of the present invention are associated. Each of the phenotypic traits can be tested using the methods described in the Examples, or using any suitable methods known in the art. Using the methods of the invention, a farmer, or feed lot operator, or the like, can group cattle according to each animal's genetic propensity for a desired trait such as circulating leptin levels, feed intake, growth rate, body weight, carcass merit and composition, and milk yield. as determined by SNP genotype, in addition to the present criteria he would ordinarily use for grouping. The cattle are tested to determine homozygosity or heterozygosity with respect to UASMS1, UASMS2, UASMS3, and EXON2-FB alleles of the ob gene so that they can be grouped such that each pen contains cattle with like genotypes.

Each pen of animals may then be fed and otherwise maintained in a manner and for a time determined by the feed lot operator to be ideal for meat production prior to slaughter, or to maximize milk production. Thus the farmer or feedlot operator is presented with opportunities for considerable efficiencies. At present, the feeder feeds all his cattle the same, incurring the same costs for each animal, and typically, with excellent management practices, perhaps 40% will grade AAA and receive the premium price for the palatability grade (depending on several other factors, such as age of animal, as we know cattle between 17-24 months of age have increased marbling compared to their younger counterparts. Approximately 55% of cattle are slaughtered at an age under 16 months, and 45% would be slaughtered at an age over 17 months). Of these, a significant number will have excess fat and will thus receive a reduced yield grade. The balance of the cattle, 60%, will grade less than AAA, and thus receive a reduced price, although the feed lot costs incurred by the operator are the same. Grouping and feeding the cattle by genotype allows the farmer to treat each group differently with a view to increasing profit.

It is contemplated that, regardless of the desirability and premium paid for any particular meat quality at any given time, providing the farmer with a more uniform group that has a predictable meat quality will provide the farmer with the opportunity to demand and receive a premium, relative to the less uniform groups of cattle presently available.

The methods of the invention are also useful in breeding programs to select for those animals having desirable phenotypes for various economically important traits, such as circulating leptin levels, feed intake, growth rate, body weight, carcass merit and composition, and milk yield. Continuous selection and breeding of animals, such as livestock, that are at least heterozygous and advantageously homozygous for a desirable polymorphism associated with, for example, improved carcass merit, would lead to a breed, line, or population having higher numbers of offspring with improved carcass merit. Thus, farmers can increase the value of their calves by using the methods of the present invention to increase the occurrence of the specific alleles in calves that are associated with economically important traits. Thus, the SNPs of the present invention can be used as selection tools in breeding programs.

The following examples are provided to describe and illustrate, but not limit, the claimed invention. Those of skill in the art will readily recognize a variety of non-critical parameters that could be changed or modified to yield essentially similar results.

EXAMPLES

Example 1

Animals and Phenotypic Data Collection

A total of 180 cattle (139 steers and 41 bulls) sired by Angus Charolais or University of Alberta Hybrid bulls were managed and tested for growth and feed efficiency under feedlot conditions. Feed intake was measured for each animal using the GrowSafe® automated feeding system (GrowSafe® Systems Ltd., Airdrie, Alberta, Canada).

Complete performance and efficiency data was available on a total of 150 animals, excluding all the bulls in test two (total of 21 animals) plus nine other animals that died or had to be excluded from the test due to health and other related problems. Weight measurements of all animals were taken weekly. The performance data analyzed include average daily gain (ADG), on-test metabolic midpoint weight (MWT), residual feed intake (RFI), feed conversion ratio (FCR), average daily dry matter intake (DMI), metabolizable energy intake per unit metabolic weight ($MEWT^{0.75}$), and partial efficiency of growth (PEG). Each animal's ADG during the test was computed as the coefficient of the linear regression of weight (kg) on time (days) using the regression procedure of SAS (SAS Institute, Inc., Cary, N.C., 1999). The MWT of each animal over the test period was computed as the midpoint $bodyweight^{0.75}$. The total feed intake of each animal over the 70 days test period was used to compute the dry matter intake (DMI) for each animal. Metabolizable energy was calculated as the product of DMI and the dietary energy content (12.14 MJ ME/kg) divided by the metabolic weight of each animal.

Residual feed intake was computed for each animal as the difference between each animal's actual feed intake from predicted expected daily feed intake based on the average daily gain and metabolic weight of each animal over the test period. Feed conversion ratio of each animal was computed as the ratio of average intake on test to average daily gain on test. Partial efficiency of growth (PEG) above maintenance of each animal was computed as the ratio of ADG to the difference between average feed intake and feed intake for maintenance.

(a) Feeding behavior data: The detection of an animal at a feedbunk by the Growsafe system starts a feeding event and ends when the time between the last two readings for the same animal was greater than 300 secs. Detection of an animal within 300 secs was considered to be one continuous feeding event. Feeding event data is then used to compute average Feeding duration (FD) is the differences between average end-time minus start-time. The feeding duration includes time spent in prehension, chewing, backing away from the bunk and chewing, socializing, scratching or licking. Feeding head down time (FHD, on the other hand, primarily includes the time associated with eating and is determined as the average number of detections of an animal during a feeding event times the system detection time of 5.7 secs.

(b) Ultrasound data: Ultrasound measurements of 12/13th rib fat depth, longissimus muscle area and marbling score were taken approximately every 28 days with an Aloka 500V real-time ultrasound with a 17 cm, 3.5-MHz linear array transducer. Each animal had five repeated ultrasound measurements, except for animals removed before the endpoint of test for metabolic studies. In this case the approximate value of the measurement was predicted from the rate of change in that trait from the previous measurements.

(c) Prediction of ultrasound measurements at constant body weight of 500 kg: There was no required weight at slaughter for Canadian Maturity I or young animals (top quality youthful carcasses) under the Canadian Beef Carcass grading system. The average slaughter weight generally ranged between 550 to 600 kg for steers to give an average hot carcass weight of about 350 to 400 kg. The final weights of the animals were below the minimum industry slaughter weight of 500 kg. However, it was desired to determine the final ultrasound measurements of backfat thickness, longissimus thoracis area and marbling score at the time the industry slaughter weight. Regression procedures were used to predict the backfat thickness, marbling score and longissimus thoracis area at a constant body weight of 500 kg.

First, the measurements for each animal (ultrasound backfat thickness, marbling score or longissimus muscle area) recorded on five consecutive periods were regressed on the body weight measured on these above dates for each animal. This yields a regression equation $Y=a+b(WT)$ for each animal, where Y is the trait value to be predicted (backfat, marbling or longissimus thoracis area), a=the intercept of the regression equation; b=the coefficient of regression and WT is the body weight of the animal (in this case set to a constant of 500 kg). Thus the equation was used to predict a value for each trait at a constant body weight of 500 kg for each animal. This resulted in the creation of a new dataset for predicted marbling, backfat or rib eye area. The new dataset was then analyzed to determine the differences between different genotypes of the different markers.

(d) Slaughter and carcass data: Of the 150 animals with complete performance data, 19 of them were bulls that were not sent to slaughter. In addition, 20 animals with extreme phenotypes for RFI were selected for metabolic measurements and no carcass data was collected on these animals. Carcass data was available for only 109 animals. Carcass traits were evaluated according to the Canadian beef carcass grading system. Standard carcass data provided under this system included slaughter weight (final liveweight), carcass weight, average backfat thickness, carcass grade fat, rib eye area, marbling quality or quality grade, marbling level and saleable meat yield. Carcass weight of each animal was determined as the weight of the left and right halves of the carcass after a 24 hrs chill at −4° C. Carcass grade fat was measured at the 12/13th rib of each carcass. Average backfat thickness was measured at two different locations along the rib eye muscle other than between the 12 and $13^{th}$ ribs. Carcass quality grade (A, AA, AAA or prime=4, 3, 2, 1 respectively) were decided according to the following criteria: animal must be physiologically less than 30 months old; meat must be bright red, firm and fine grained; muscling must range from good (with no deficiencies) to excellent; gradefat must be firm and white (or amber) and not less than 2 mm at the site of measurement ($12/13^{th}$ rib).

To score A, AA, AAA or prime is not directly dependent on the marbling level. Associated with each of these quality grades is a score for marbling level (ranges from 0 to 90 such as A0, A50, AA10, AAA0, AAA40 etc). To obtain a quantitative value for marbling therefore, the quality grade and marbling level of each graded carcass are combined to compute a value for marbling score according to the equation: marbling score=(QG+ML)/100, where QG is the quality grade (100, 200, 300 and 400 for A, AA, AAA, and prime, respectively) and ML is marbling level and ranges from 0 to 90 in units of 10. Marbling score is a measure of intramuscular fat of the ribeye muscle and can be classified as 1 to <2 units=trace marbling (Canada A quality grade); 2 to <3 units=slight marbling (Canada AA quality grade); 3 to <4 units=small to moderate marbling (Canada AAA quality grade) and $\geq 4$ units=slightly abundant or more marbling (Canada Prime). Lean meat yield is an estimate of saleable meat and was calculated according to the equation: Lean meat yield %=57.96+(0.202×L. thoracis area, $cm^2$)−(0.027×warm carcass weight, kg)−(0.703×average backfat thickness, mm). The lean meat yield of the carcass may be used to assign a grade (yield grade) to each animal according to Y1=$\geq$59%, Y2=54 to <59% and Y3=<54%.

Example 2

Blood Sampling, DNA Extraction and SNP Detection

Blood samples were collected from each animal at start of the feed intake test from which genomic DNA was extracted using a modified saturated salt phenol/chloroform procedure (Sambrook et al., 1989). Identification of polymorphisms in the bovine leptin promoter utilized SEQ ID NO: 1 (GenBank accession number AB070368, Taniguchi et al., 2002). Genomic DNA from a panel of 16 animals was amplified by polymerase chain reaction using forward and reverse primers designed to cover the entire bovine leptin promoter region. The PCR products from each animal were sequenced on a Beckman CEQ 8000 Genetic Analysis System (Beckman Coulter Instruments, Inc.). Sequence data for each animal were analyzed to identify putative single nucleotide polymorphisms.

The analysis identified three new single nucleotide polymorphisms (SNPs), namely UASMS1, UASMS2 and UASMS3 located, respectively at positions 207 (C/T substitution), 528 (C/T substitution) and 1759 (C/G substitution) (Numbering is that of SEQ ID NO: 1, GenBank accession number AB070368). The exon 2 SNP identified by Buchanan et al. (2002) is located at position 305 (C/T missence mutation) (GenBank accession No. AY138588). The genotyping of each leptin gene-specific polymorphism was carried out using the 5' nuclease allelic discrimination assay on an ABI PRISM™ 7700 sequence detector (Applied Biosystems Inc.). Forward and reverse primers (Table 1) were designed to amplify each polymorphism using genomic DNA from each animal. Additionally, two ABI TaqMan® fluorogenic probes (with a different reporter dye on each probe) were designed to target the two alleles of each SNP (Table 1).

dom animal additive effects. Animal was fitted as a random effect to account for background genes. Start weight of animal on test, age of dam or age of animal on test were included

TABLE 1

Position, primer and probe information for genotyping each polymorphism

| SNP | Position[a] | Forward Primer | Forward Primer | Probe 1[c] | Probe 2[c] |
|---|---|---|---|---|---|
| UASMS1[a] | 207 (C/T) | ggcacaatcctgtgtat tggtaaga | ggcacaatcctgtgtat tggtaaga | ctttcacctagtatatctag | tctttcacctagtatgtctag |
| UASMS2[a] | 528 (C/T) | aggtgcccagggactca | aggtgcccagggactca | caagctctagagcctgtgt | aagctctagagcctatgt |
| UASMS3[a] | 1759 (C/G) | atgtatattttggtgtg agagtgtgtgt | atgtatattttggtgtg agagtgtgtgt | cacacattccaatcaa | cacattgcaatcaa |
| EXON2-FB[b] | 305 (C/T) | ggctttggccctatctg tcttac | ggctttggccctatctg tcttac | ccttgcagatggg | ccttgcggatggg |

Forward Primer columns discloses SEQ. ID NOS.: 7, 11, 15 and 19, respectively in order of appearance. Probe 1 column discloses SEQ ID NOS.: 9, 14, 17 and 21, respectively, in order of appearance. Probe 2 column discloses SEQ ID NOS.: 10, 13, 18 and 22, respectively, in order of appearance
[a] Positions are designated according to SEQ ID NO.: 1 GenBank accession number AB070368.
[a] Position is designated according to SEQ ID NO.: 5 (GenBank accession number AY138588)
[a] Nucleotides in bold target the specific alleles of the SNP A subset of the genotyped animals was sequenced across each polymorphism and the sequence results were used to confirm the genotypes obtained by discrimination assays. In addition to the experimental herd, a total of 160 animals from five commercial lines of relatively unrelated cattle (Beef-Booster genetic selection lines M1, M2, M3, M4, and TX) were also genotyped and the allele frequencies of the SNPs were determined in these animals. Foundation breed(s) were Angus for M1, Hereford for M2, various small breeds for M3, Limousin and Gelbvieh for M4, and Charolais for TX (Kress, D. D., Davis K. C. and Tess, M. W. (1996) Adjusting scrotal circumference of yearling beef bulls in five composites, *Canadian Journal of Animal Science* 76: 189-191).

Chi-square tests were used to examine the genotype frequencies of each polymorphism for deviations from Hardy-Weinberg equilibrium for both the experimental and commercial populations. Differences among the various selection lines of the commercial herd in allele frequencies of the polymorphisms were also tested by chi-square analyses using the Categorical Model Procedure of SAS (SAS Institute, Inc., Cary, N.C., 1999). Single marker associations were then carried out to evaluate the relationship of the different marker genotypes of each marker on serum leptin concentration, growth rate, body weight, feed intake, feed efficiency and ultrasound traits. The data was analyzed using PROC MIXED of SAS (SAS Institute, Inc., Cary, N.C., 1999). The statistical model used included fixed effects of SNP genotype, test group (one and two), sex of animal (bull and steer) and ranin the model as linear covariates. The model used to analyze the carcass data was similar to that of the live animal data but excluded the fixed effects of sex as only steers were sent to slaughter. Associations between different polymorphisms and carcass quality grade were tested by chi-square analyses using the Categorical Model Procedure of SAS (SAS Institute, Inc., Cary, N.C., 1999).

Additive genetic effects were estimated for traits that were significantly different ($P<0.10$) between animals with different SNP genotypes. Significant additive genetic (a) effects were computed by subtracting the solution of the estimate for the trait effect of the two homozygote genotypes. We also estimated dominance deviation (d) as the deviation of the CT genotypic value from the midpoint between the TT and CC genotypic values.

Example 3

Genotype and Allele Frequencies

Tables 2 and 3 show the genotype frequencies and chi-square tests of Hardy-Weinberg equilibrium for the different polymorphisms in the experimental and commercial populations, respectively. Observations of the genotypes revealed that all animals that had genotypes CC, CT or TT of UASMS1 also had genotypes CC, CG or GG of UASMS 3, respectively. Thus, the two polymorphisms were in complete linkage disequilibrium and were designated together as UASMS1-3. The T-G alleles of UASMS1-3 were 59% each in the experimental population and the T alleles of UASMS2 were 21% and EXON2-FB 44%. Similarly, the frequencies of the T-G or T alleles of UASMS1-3, UASMS2 and EXON2-FB were 48%, 20% and 53%, respectively, in the commercial population. Chi-square analyses between observed and expected genotypes showed that the frequencies of all the genotypes of all three polymorphisms did not deviate significantly from Hardy-Weinberg proportions in both populations ($P>0.10$).

TABLE 2

Genotype frequencies and chi-square tests of Hardy-Weinberg equilibrium of the three markers in the experimental population

| Polymorphism | CC/CC | CT/CG | TT/GG | TOTAL | % T-G | Chi-square[z] | p-value[y] |
|---|---|---|---|---|---|---|---|

TABLE 2-continued

Genotype frequencies and chi-square tests of Hardy-Weinberg equilibrium of the three markers in the experimental population

| UASMS1-3 | 33 | 82 | 65 | 180 | 0.59 | 0.63 | 0.73 |
|---|---|---|---|---|---|---|---|
| Polymorphism | CC | CT | TT | TOTAL | % T | Chi-square | p-value |
| UASMS2 | 113 | 58 | 9 | 180 | 0.21 | 0.19 | 0.91 |
| Polymorphism | CC | CT | TT | TOTAL | % T | Chi-square | p-value |
| EXON2-FB | 59 | 84 | 37 | 180 | 0.44 | 0.50 | 0.78 |

[z]Degree of deviation of observed genotype frequencies from expectations
[y]Probability of a significant chi-square value.

TABLE 3

Genotype frequencies and chi-square tests of Hardy-Weinberg equilibrium of the three markers in the commercial population

| Polymorphism | CC/CC | CT/CG | TT/GG | TOTAL[x] | % T-G | Chi-square[z] | P value[y] |
|---|---|---|---|---|---|---|---|
| UASMS1-3 | 41 | 84 | 35 | 160 | 0.48 | 0.42 | 0.81 |
| Polymorphism | CC | CT | TT | TOTAL | % T | Chi-square | p-value |
| UASMS2 | 100 | 55 | 5 | 160 | 0.20 | 0.61 | 0.74 |
| Polymorphism | CC | CT | TT | TOTAL | % T | Chi-square | p-value |
| EXON2-FB | 32 | 86 | 43 | 161 | 0.53 | 0.87 | 0.65 |

[z]Degree of deviation of observed genotype frequencies from expectations
[y]Probability of a significant chi-square value.
[x]The total population size is 162 animals. Two samples failed to amplify for UASMS1, 2 and 3 and one sample failed to amplify for EXON2-FB.

Table 4 shows the frequencies of the different polymorphisms in the different strains of the commercial population. Frequencies of the T-G alleles of UASMS1-3 differed among the different lines of the commercial population (P<0.05, $\chi^2$=9.17) and were lower in the M1 line (Angus) compared to TX (Charolais) (P<0.004, $\chi^2$=8.10), M2 (Hereford) (P<0.10, $\chi^2$=2.86), M3 (various small breeds) (P<0.02 $\chi^2$=5.48) and M4 (Gelbvieh and Limousin) (P<0.04, $\chi^2$=4.10).

hd a higher frequency of the T allele of EXON2-FB compared to the lines based on (Gelbvieh and Limousin (M4) ($\chi^2$=5.41, P<0.05) and Charolais (TX) ($\chi^2$=P<0.01) and tended to be higher than line based on various small breeds (M3) ($\chi^2$=3.82, P<0.10), but not Hereford (M2) (P>0.10). The allele frequency of EXON2-FB did not differ among the other selection lines of the commercial population (P>0.10).

TABLE 4

Genotype and allele frequencies of the various markers in five strains of a commercial population of cattle

| | | UASMS1-3 | | | T-G | UASMS2 | | | T | EXON2-FB | | | T |
|---|---|---|---|---|---|---|---|---|---|---|---|---|---|
| Line | Animals | CC/CC | CT/CG | TT/GG | allele | CC | CT | TT | allele | CC | CT | TT | allele |
| M1 | 31 | 13 | 16 | 2 | 0.32[a] | 24 | 7 | 0 | 0.11[a] | 2 | 16 | 14 | 0.69[a] |
| M2 | 33 | 8 | 19 | 6 | 0.47[b] | 19 | 11 | 3 | 0.26[b] | 7 | 15 | 11 | 0.56[ab] |
| M3 | 31 | 7 | 15 | 9 | 0.53[b] | 18 | 12 | 1 | 0.23[b] | 6 | 18 | 7 | 0.52[b] |
| M4 | 33 | 7 | 19 | 7 | 0.50[b] | 23 | 9 | 1 | 0.17[ab] | 6 | 22 | 5 | 0.48[b] |
| TX | 32 | 6 | 15 | 11 | 0.58[b] | 16 | 16 | 0 | 0.25[b] | 11 | 15 | 6 | 0.42[b] |

[a,b,c]Allele frequencies of UASMS1-3 (P = 0.01, $\chi^2$ = 9.17), UASMS2 (P<0.05, $\chi^2$ = 5.71) and EXON2-FB (P<0.04, $\chi^2$ = 9.93) in columns followed by different superscripts are different.

Frequency of the T allele of UASMS2 differed among selection lines (P<0.05, $\chi^2$=5.71) and was higher for M1 compared to M2 (P<0.05, $\chi^2$=4.19), M3 (P<0.10, $\chi^2$=2.71) and TX (P<0.05, $\chi^2$=3.79). Differences in allele frequency of UASMS2 in the other strains were not significant (P>0.10). There were differences in allele frequencies of EXON2-FB among selection lines of the commercial population (P<0.041, $\chi^2$=9.93). The Angus-based selection line (M1)

Example 4

Associations of UASMS1-3 with Various Phenotypic Traits

Table 5 and shows the effect of different genotypes of UASMS1-3 on measures of serum leptin concentration, performance, feed efficiency and feeding behavior in the experimental population. Metabolic weight was higher (P<0.01) for animals with genotype TT-GG than for CC-CC (additive effect, a=−5.35±1.65 kg $^{0.75}$). Average daily gain tended to be higher (P<0.10) for animals with genotype TT-GG than for animals with genotype CC-CC (additive effect, a=−0.12±0.04 kg d$^{−1}$). Dry matter intake was significantly higher (additive effect, a=−0.88±0.24 kg d$^{−1}$) (P=0.001) and metabolizable energy per metabolic weight tended to differ (P<0.10) [additive effect, a=−49.06±23.60 KJ (kg$^{0.75}$d)$^{−1}$] among animals with different genotypes of UASMS1-3. However, serum leptin concentration, feed conversion ratio, residual feed intake and partial efficiency of growth did not show any significant associations with genotypes of UASMS1-3 (P>0.10). For the feeding behavior traits, feeding duration was different (P=0.04) (additive effect, a=−7.66±2.58 min d$^{−1}$,) among animals with different genotypes of UASMS1-3. On the other hand, feeding frequency tended to be lower (P<0.10) (additive effect, a=3.32±1.07 events d$^{−1}$,) for animals with genotype TT-GG than for CC-CC.

TABLE 5

Effect of different genotypes of UASMS1-3 (least-squares means ± standard error) on measures of serum leptin, performance, efficiency and feeding behavior

| Trait | UASMS1-3 Marker genotype[z] | | | P value[y] |
| --- | --- | --- | --- | --- |
| | CC-CC | CT-CG | TT-GG | |
| Number of animals | 27 | 68 | 55 | |
| Serum leptin, performance and efficiency | | | | |
| Serum leptin level, ng ml$^{−1}$ | 12.48 ± 1.41 | 12.13 ± 0.96 | 13.26 ± 1.00 | 0.60 |
| Metabolic mid-weight, kg$^{.75}$ | 83.79 ± 1.61 | 85.62 ± 1.10 | 89.14 ± 1.13 | 0.002 |
| Average daily gain, kg d$^{−1}$ | 1.29 ± 0.05 | 1.38 ± 0.04 | 1.42 ± 0.04 | 0.08 |
| Residual feed intake, kg d$^{−1}$ | −0.53 ± 0.59 | −0.37 ± 0.57 | −0.20 ± 0.58 | 0.25 |
| Feed conversion ratio | 6.04 ± 0.18 | 5.95 ± 0.13 | 6.11 ± 0.13 | 0.57 |
| Dry matter intake, kg d$^{−1}$ | 7.17 ± 0.23 | 7.59 ± 0.16 | 8.05 ± 0.16 | 0.001 |
| ME intake, KJ kg$^{0.75}$ d$^{−1}$ | 1034.3 ± 24.1 | 1073.26 ± 16.3 | 1093.4 ± 24.1 | 0.07 |
| Partial Efficiency of growth, | 0.34 ± 0.01 | 0.34 ± 0.01 | 0.32 ± 0.01 | 0.15 |
| Feeding Behavior | | | | |
| Feeding duration, min d$^{−1}$ | 50.25 ± 2.27 | 52.66 ± 1.55 | 56.27 1.61 | 0.04 |
| Head down time, min d$^{−1}$ | 34.72 ± 2.25 | 36.76 ± 1.53 | 38.41 ± 1.59 | 0.29 |
| Feeding frequency, events d$^{−1}$ | 34.06 ± 1.07 | 31.85 ± 0.92 | 30.74 ± 1.01 | 0.08 |

[z]UASMS1-3 are located at positions 207 (C/T substitution) and 1759 (C/G substitution) in the bovine leptin promoter according to SEQ ID NO: 1 (AB070368)
[y]P value = probability of differences among different marker genotypes.

Table 6 shows the body weight, ultrasound and carcass measurements of animals with different UASMS1-3 genotypes. Average body weight (additive effect, a=−29.73±10.49 kg), final live weight (additive effect, a=−33.39±11.80) (P<0.01), slaughter weight (additive effect, a=37.07±13.79 kg) and carcass weight (additive effect, a=−18.49±8.59 kg) (P=0.01) were higher in animals with the TT-GG than for CC-CC genotype of UASMS1-3. With the exception of final ultrasound backfat thickness, which was higher in animals with genotypes TT-GG than for CC-CC (P<0.05), there were no differences among genotypes in the different ultrasound measurements (P>0.10). In addition, carcass grade fat, backfat thickness, longissimus muscle area, marbling score and lean meat yield did not differ among different UASMS1-3 genotypes. Categorical data analysis of the carcass grades (A, AA, AAA) among genotypes of UASMS1-3 showed no significant associations between quality grade and genotypes ($\chi^2$=1.37, P=0.50) (Table 11).

TABLE 6

Effect of different genotypes of UASMS1-3 (least-squares means ± standard error) on measures of body weight, ultrasound and carcass merit of hybrid cattle

| Trait | UASMS1-3 Marker genotype[z] | | | P value[y] |
| --- | --- | --- | --- | --- |
| | CC-CC | CT-CG | TT-GG | |
| Number of animals | 27 | 68 | 55 | |
| Weight and ultrasound Initial Measurements (Jan 10) | | | | |
| Body weight, kg | 335.24 ± 8.88 | 339.51 ± 6.09 | 355.12 ± 6.25 | 0.03 |
| Ultrasound backfat, mm | 5.54 ± 0.53 | 5.10 ± 0.47 | 5.13 ± 0.49 | 0.15 |
| Ultrasound marbling score | 4.25 ± 0.33 | 4.34 ± 0.32 | 4.31 ± 0.33 | 0.68 |

TABLE 6-continued

Effect of different genotypes of UASMS1-3 (least-squares means ± standard error) on measures of body weight, ultrasound and carcass merit of hybrid cattle

| Trait | UASMS1-3 Marker genotype[z] | | | P value[y] |
|---|---|---|---|---|
| | CC-CC | CT-CG | TT-GG | |
| Longissimus thoracis area, cm² | 64.05 ± 1.15 | 62.88 ± 0.79 | 61.95 ± 0.82 | 0.22 |
| Final Measurements (May 01) | | | | |
| Body weight, kg | 477.46 ± 11.60 | 485.24 ± 7.96 | 510.86 ± 8.16 | 0.005 |
| Ultrasound backfat | 5.84 ± 0.91 | 5.41 ± 0.84 | 6.45 ± 0.88 | 0.04 |
| Ultrasound marbling score | 4.56 ± 0.12 | 4.63 ± 0.08 | 5.69 ± 0.09 | 0.61 |
| Longissimus thoracis area, cm² | 74.71 ± 1.35 | 73.22 ± 0.92 | 73.45 ± 0.96 | 0.53 |
| Average Measurements[x] | | | | |
| Body weight, kg | 402.90 ± 10.24 | 412.35 ± 7.02 | 432.64 ± 6.20 | 0.01 |
| Ultrasound backfat | 5.72 ± 0.61 | 5.26 ± 0.55 | 5.83 ± 0.57 | 0.17 |
| Ultrasound marbling score | 4.39 ± 0.10 | 4.47 ± 0.07 | 4.67 ± 0.08 | 0.76 |
| Longissimus thoracis area, cm² | 69.32 ± 0.87 | 68.02 ± 0.59 | 67.93 ± 0.62 | 0.26 |
| Carcass Traits | | | | |
| Number of animals | 22 | 49 | 38 | |
| Slaughter weight, kg | 490.6 ± 10.9 | 501.2 ± 7.3 | 527.65 ± 8.31 | 0.01 |
| Carcass weight, kg | 287.8 ± 6.8 | 286.62 ± 4.53 | 306.31 ± 5.18 | 0.01 |
| Grade Fat, mm | 9.52 ± 0.71 | 8.11 ± 0.48 | 9.29 ± 0.54 | 0.15 |
| Ave. Backfat, mm | 10.96 ± 0.75 | 9.67 ± 0.50 | 10.81 ± 0.57 | 0.21 |
| Carcass marbling score | 2.32 0.38 | 2.11 ± 0.38 | 2.29 ± 0.39 | 0.18 |
| L. thoracis area, cm² | 75.45 ± 1.39 | 76.58 ± 0.92 | 76.63 ± 1.09 | 0.77 |
| Lean meat yield, % | 57.52 ± 0.75 | 58.86 ± 0.50 | 57.93 ± 0.59 | 0.25 |

[z]UASMS1-3 polymorphism are located at positions 207 (C/T substitution) and 1759 (C/G substitution) in the bovine leptin promoter according to SEQ ID NO: 1 (AB070368)
[y]P value = probability of differences among different marker genotypes.
[x]Average of five measurements taken between January 10 and May 01 at approximately monthly intervals Example 5

Associations of UASMS2 with Various Phenotypic Traits

The effect of different genotypes of UASMS2 on measures of serum leptin concentration, performance, feed efficiency and ultrasound and carcass merit are presented in Tables 7 and 8. The T allele of UASMS2 was highly significantly associated with serum leptin concentration (P<0.0001), and was higher for animals with genotype TT than for CC (additive effect, a=−11.79±2.76 ng ml$^{-1}$). Serum leptin was also higher (P=0.04) in CT animals than in CC animals (dominance deviation, d=−3.38±1.81 ng ml$^{-1}$). Metabolic weight differed among genotypes (P<0.05) and was higher for animals with genotype TT than for CC (additive effect, a=−6.01±2.50 kg$^{0.75}$). Average daily gain was significantly different (P<0.01) among genotypes and was higher for animals with genotype TT than for animals with genotype CC (additive effect, a=−0.15±0.04 kg d$^{-1}$).

TABLE 7

Effect of different genotypes of UASMS2 (least-squares means ± standard error) on measures of serum leptin, performance, efficiency and feeding behavior hybrid cattle

| Trait | UASMS2 Marker genotype[z] | | | P value[z] |
|---|---|---|---|---|
| | CC | CT | TT | |
| Number of animals | 99 | 45 | 6 | |
| Serum leptin, performance and efficiency | | | | |
| Serum leptin level, ng ml$^{-1}$ | 11.92 ± 0.93 | 14.43 ± 1.24 | 23.71 ± 2.80 | <0.0001 |
| Metabolic mid-weight, kg$^{.75}$ | 85.77 ± 1.09 | 88.19 ± 1.20 | 92.14 ± 3.04 | 0.03 |
| Average daily gain, kg d$^{-1}$ | 1.32 ± 0.03 | 1.47 ± 0.04 | 1.46 ± 0.10 | 0.002 |
| Residual feed intake, kg d$^{-1}$ | −0.71 ± 0.23 | −0.41 ± 0.23 | −0.95 ± 0.40 | 0.09 |
| Feed conversion ratio | 6.06 ± 0.12 | 5.95 ± 0.13 | 5.82 ± 0.34 | 0.63 |
| Dry matter intake, kg d$^{-1}$ | 7.44 ± 0.15 | 8.13 ± 0.17 | 7.89 ± 0.43 | 0.001 |
| ME intake, KJ kg$^{0.75}$ d$^{-1}$ | 1061.1 ± 15.9 | 1110.1 ± 18.2 | 1047.3 ± 48.9 | 0.04 |
| Partial Efficiency of growth, | 0.34 ± 0.01 | 0.33 ± 0.01 | 0.36 ± 0.02 | 0.64 |
| Feeding Behavior | | | | |
| Feeding duration, min d$^{-1}$ | 49.69 ± 3.39 | 54.89 ± 3.31 | 49.96 ± 5.39 | 0.02 |
| Head down time, min d$^{-1}$ | 34.26 ± 3.17 | 37.17 ± 3.10 | 29.84 ± 5.11 | 0.01 |
| Feeding frequency, events d$^{-1}$ | 33.12 ± 1.87 | 30.86 ± 1.86 | 28.64 ± 3.34 | 0.09 |

[z]UASMS2 polymorphism is a C/T substitution located at position 528 of the bovine leptin promoter according to SEQ ID NO: 1 (AB070368)
[y]P value = probability of differences among different marker genotypes.

TABLE 8

Effect of different genotypes of UASMS2 (least-squares means ± standard error) on measures of body weight, ultrasound and carcass merit of hybrid cattle

| Trait | UASMS2 Marker genotype[z] | | | P value[y] |
|---|---|---|---|---|
| | CC | CT | TT | |
| Number of animals | 99 | 45 | 6 | |
| Body weight and ultrasound Initial Measurements (Jan 10) | | | | |
| Body weight, kg | 339.93 ± 5.95 | 352.53 ± 6.54 | 363.26 ± 16.59 | 0.01 |
| Ultrasound backfat, mm | 4.38 ± 0.25 | 4.61 ± 0.27 | 5.64 ± 0.68 | 0.15 |
| Ultrasound marbling score | 4.32 ± 0.08 | 4.46 ± 0.08 | 4.56 ± 0.21 | 0.15 |
| Longissimus thoracis area, cm$^2$ | 62.97 ± 0.76 | 62.17 ± 0.82 | 60.13 ± 2.13 | 0.32 |
| Final Measurements (May 01) | | | | |
| Body weight, kg | 488.33 ± 7.86 | 502.86 ± 8.64 | 530.35 ± 21.93 | 0.07 |
| Ultrasound backfat | 5.20 ± 0.35 | 6.43 ± 0.38 | 9.51 ± 0.96 | <0.0001 |
| Ultrasound marbling score | 4.61 ± 0.09 | 4.79 ± 0.10 | 5.52 ± 0.25 | 0.001 |
| Longissimus thoracis area, cm$^2$ | 74.03 ± 0.09 | 72.64 ± 0.10 | 68.43 ± 2.48 | 0.05 |
| Average Measurements[x] | | | | |
| Body weight, kg | 413.34 ± 6.93 | 427.65 ± 7.62 | 443.68 ± 19.32 | 0.10 |
| Ultrasound backfat | 4.83 ± 0.26 | 5.43 ± 0.28 | 7.12 ± 0.73 | 0.003 |
| Ultrasound marbling score | 4.41 ± 0.08 | 4.58 ± 0.08 | 5.02 ± 0.21 | 0.006 |
| Longissimus thoracis area, cm$^2$ | 68.37 ± 0.57 | 67.77 ± 0.62 | 64.34 ± 1.60 | 0.04 |
| Predicted @ 500 kg BW | | | | |
| Ultrasound backfat | 5.34 ± 0.32 | 6.21 ± 0.34 | 8.65 ± 0.88 | 0.0002 |
| Ultrasound marbling score | 4.57 ± 0.40 | 4.77 ± 0.40 | 5.36 ± .46 | 0.002 |
| Longissimus thoracis area, cm$^2$ | 74.65 ± 0.79 | 73.06 ± 0.86 | 70.21 ± 2.19 | 0.05 |
| Carcass data | | | | |
| Number of animals | 76 | 29 | 4 | |
| Slaughter weight, kg | 500.9 ± 6.0 | 516.7 ± 9.9 | 537.27 ± 26.2 | 0.20 |
| Carcass weight, kg | 290.6 ± 3.8 | 299.4 ± 6.2 | 295.9 ± 16.5 | 0.48 |
| Grade Fat, mm | 8.34 ± 0.43 | 9.54 ± 0.70 | 10.91 ± 1.84 | 0.16 |
| Ave. Backfat, mm | 9.76 ± 0.44 | 11.50 ± 0.71 | 12.09 ± 1.92 | 0.08 |
| Carcass marbling score | 2.26 ± 0.07 | 2.42 ± 0.11 | 2.71 ± 0.30 | 0.20 |
| L. thoracis area, cm$^2$ | 76.08 ± 0.75 | 77.30 ± 1.22 | 74.63 ± 3.32 | 0.61 |
| Lean meat yield, % | 58.62 ± 0.41 | 57.39 ± 0.65 | 56.90 ± 1.77 | 0.22 |

[z]UASMS2 polymorphism is a C/T substitution located at position 528 of the bovine leptin promoter according to SEQ ID NO: 1 (AB070368)
[y]P value = probability of differences among different marker genotypes.
[x]Average of five measurements taken between January 10 and May 01 at approximately monthly intervals Dry matter intake was significantly different (P=0.001) among genotypes of UASMS2 and was higher in animals with TT compared to CC (additive effect, a=−0.45±0.19 kg d$^{-1}$) and CT compared to CC (dominance effect, d=−0.69±0.26 kg d$^{-1}$). Metabolizable energy per metabolic weight also differed among genotypes of UASMS2 (P=0.04) and was higher in CT compared to TT or CC (dominance deviation, d=−56.11±25.24 KJ (kg$^{0.75}$ d)$^{-1}$ UASMS2. The higher DM intake of animals with the T allele observed in this study is surprising as it would generally be expected that the animals with higher body fat and significantly higher serum leptin would have decreased feed consumption. It may be argued that this result may be due to the fact that there were only very few animals available with genotype TT for comparison (as seen by the high standard errors associated with the trait values of TT animals). However, the results also showed that feed intake was higher in heterozygous animals, indicating that the T allele of UASMS2 is in fact associated with increased feed intake.

Recent data from daily cows (Liefers et al., 2003) show that cows with higher dry matter intake were significantly heavier and had significantly higher serum leptin concentration. In addition, these authors also showed that cows with a negative energy balance (strongly related to lower body weight and lower body condition) had significantly lower serum leptin concentration compared to positive energy balance cows. In the present data serum leptin concentration is positively related to feed intake (r=0.26) and body weight (r=0.25), thus confirming the findings by Liefers et al. (2003). It has been observed in mice that obviously obese mice with higher serum leptin still continued to eat more (Houseknecht et al., 1998). Evidence in the literature shows that response to the inhibitory feedback effects of leptin is more sensitive in leaner animals, and sensitivity is greatly reduced in animals with large fat stores (cattle generally have higher body fat content reminiscent of obesity in other species), even though circulating concentrations of leptin in the latter group are high (Houseknecht et al., 1998). Perhaps, the findings of this study may form the basis of leptin resistance in cattle. This phenomenon of leptin-resistance in certain obese individuals is not-yet clearly understood, though it has been suggested that some of the leptin receptor forms may be involved in incidence of leptin resistance (Houseknecht et al., 1998).

Average backfat thickness (additive effect, a=−2.29±0.50 mm); final backfat thickness (additive effect, a=−4.31±0.95 mm); and ultrasound backfat thickness were significantly higher (P<0.001) for animals with the T allele of UASMS2 than for animals with the C allele. Similarly, the T allele of UASMS2 was significantly associated with higher (P<0.01) average ultrasound marbling score (additive effect, a=−0.61±0.21) and final marbling score (additive effect, a=−0.89±0.25, P<0.01) compared to the C allele. These results are not surprising as the correlation between ultrasound marbling and backfat thickness in the present data set was also high (r=0.54) (data not shown). Taken to a constant body weight of 500 kg through linear regression predictions, animals with the TT genotype of UASMS2 had significantly higher ultrasound backfat (P<0.001) and marbling scores (P<0.01) compared to animals with the CC genotypes. The significant increases in body fatness in animals with the T allele of UASMS2 was associated with slight reductions (P<0.05) in final (additive effect, a=5.60±2.50 cm$^2$,) and average (additive effect, a=4.03±1.58 cm$^2$) longissimus thoracis area. Measures of carcass weight and body fat were generally higher in animals with the T allele compared to the C allele. However, there were only a few animals with the TT genotype that had carcass data for comparison and thus there were no statistical differences among genotypes of UASMS2 in these carcass traits. The opposite is true with carcass measures of lean meat yield and longissimus muscle area. Categorical data analysis of the carcass grades (A, AA, and AAA) among genotypes of UASMS2 showed no significant associations between quality grade and genotypes ($\chi^2$=1.14, P=0.56) (Table 11).

Residual feed intake tended to differ (P<0.10) among UASMS2 genotypes and was lower in CT (dominance effect, d=0.42±0.21 kg d$^{-1}$) than in the homozygotes. Feed conversion ratio and partial efficiency of growth did not differ (P>0.30) among genotypes of UASMS2. The present data also did not show statistical significance in final weight, mean body weight, slaughter weight and carcass weight among animals with different UASMS2 genotypes (obviously due to the very few TT animals available for comparison and associated with high standard errors of genotype means). However, the T allele was generally associated with higher body weights with differences between TT and CC animals in mean body weight, final weight and slaughter weight of 30.34 kg, 42.02 kg and 36.37 kg, respectively. Feeding duration (dominance effect, d=5.07±2.61 min d$^{-1}$) and feeding head down time (dominance effect, d=5.12±2.51 min d$^{-1}$) differed among genotypes and were higher in heterozygotes of UASMS2 than homozygotes (P<0.05). Feeding frequency tended to differ among genotypes (P<0.10) among genotypes of UASMS2 and was higher for CC animals than for TT animals (additive effect, a=4.47±2.86 events d$^{-1}$).

Example 6

Associations of EXON2-FB with Various Phenotypic Traits

The effect of different genotypes of EXON2-FB on measures of serum leptin concentration, performance, feed efficiency, feeding behavior and ultrasound and carcass merit are presented in Tables 9 and 10. Metabolic midpoint weight was lower (P<0.05) for animals with genotype TT than for CC (additive effect, a=4.16±1.61 kg$^{0.75}$). Average daily gain tended to differ among genotypes (P<0.10) and was lower in TT animals compared to CC animals (additive effect, a=0.12±0.05 kg d$^{-1}$). Average backfat thickness (additive effect, a=−0.56±0.19 mm) and final ultrasound backfat (additive effect, a=−1.07±0.17 mm) were lower (P<0.05) for animals with genotype CC than for TT (Buchanan et al., 2002). Feeding duration tended to differ (P=0.08) among genotypes of EXON2-FB and was higher for CC animals than for CT animals (dominance deviation, a=−2.71±1.63 events d$^{-1}$). Feeding frequency was different (P=0.01) among genotypes of EXON2-FB and was higher for TT animals than for CT animals (dominance deviation, a=−2.66±1.11 events d$^{-1}$) or CC animals (additive effect, a=−3.30±1.51 events d$^{-1}$).

TABLE 9

Effect of different genotypes of EXON2-FB (least-squares means ± standard error) on measures of serum leptin, performance, efficiency and feeding behavior of hybrid cattle

| Trait | EXON2-FB Marker genotype[z] | | | P value[y] |
|---|---|---|---|---|
| | CC | CT | TT | |
| Number of animals | 50 | 68 | 32 | |
| Serum leptin, performance and efficiency | | | | |
| Serum leptin level, ng ml$^{-1}$ | 13.69 ± 1.13 | 12.86 ± 0.99 | 13.02 ± 1.43 | 0.78 |
| Metabolic mid-weight, kg$^{.75}$ | 88.93 ± 1.24 | 86.17 ± 1.07 | 84.77 ± 1.57 | 0.02 |
| Average daily gain, kg d$^{-1}$ | 1.43 ± 0.04 | 1.36 ± 0.04 | 1.32 ± 0.05 | 0.07 |
| Residual feed intake, kg d$^{-1}$ | −0.44 ± 0.24 | −0.63 ± 0.24 | −0.61 ± 0.27 | 0.40 |
| Feed conversion ratio | 6.07 ± 0.14 | 6.01 ± 0.12 | 6.08 ± 0.18 | 0.89 |
| Dry matter intake, kg d$^{-1}$ | 7.73 ± 0.53 | 7.51 ± 0.53 | 7.45 ± 0.54 | 0.21 |
| ME intake, KJ kg$^{0.75}$ d$^{-1}$ | 1069.3 ± 62.7 | 1041.2 ± 62.9 | 1035.5 ± 64.4 | 0.22 |
| Partial Efficiency of growth, | 0.33 ± 0.02 | 0.34 ± 0.02 | 0.33 ± 0.02 | 0.50 |
| Feeding Behavior | | | | |
| Feeding duration, min d$^{-1}$ | 56.19 ± 7.40 | 52.05 ± 7.46 | 52.96 ± 7.58 | 0.08 |
| Head down time, min d$^{-1}$ | 36.44 ± 3.24 | 33.19 ± 3.09 | 33.55 ± 3.35 | 0.18 |
| Feeding frequency, events d$^{-1}$ | 32.04 ± 1.88 | 31.03 ± 1.81 | 35.34 ± 2.08 | 0.01 |

[z]EXON2-FB polymorphism is a C/T substitution located at position 305 of exon 2 of the bovine leptin gene according to SEQ ID NO: 5 (Gen bank accession no. AY138588 - Buchanan et al., 2002).
[y]P value = probability of differences among different marker genotypes

TABLE 10

Effect of different genotypes of EXON2-FB (least-squares means ± standard error) on measures of body weight, ultrasound and carcass merit of hybrid cattle

| Trait | EXON2-FB Marker genotype[z] | | | P value[y] |
|---|---|---|---|---|
| | CC | CT | TT | |
| Number of animals | 50 | 68 | 32 | |
| *Body weight and ultrasound data* | | | | |
| *Initial Measurements (Jan 10)* | | | | |
| Body weight, kg | 353.99 ± 6.68 | 341.70 ± 5.84 | 337.74 ± 8.47 | 0.12 |
| Ultrasound backfat, mm | 4.37 ± 0.27 | 4.72 ± 0.23 | 5.00 ± 0.34 | 0.17 |
| Ultrasound marbling score | 4.36 ± 0.03 | 4.35 ± 0.03 | 4.31 ± 0.04 | 0.47 |
| Longissimus thoracis area, cm$^2$ | 61.90 ± 0.37 | 61.72 ± 0.32 | 61.69 ± 0.46 | 0.91 |
| *Final Measurements (May 01)* | | | | |
| Body weight, kg | 510.43 ± 8.73 | 489.68 ± 7.63 | 480.11 ± 11.07 | 0.02 |
| Ultrasound backfat | 6.40 ± 0.15 | 6.90 ± 0.13 | 7.47 ± 0.19 | 0.03 |
| Ultrasound marbling score | 4.98 ± 0.09 | 4.96 ± 0.07 | 5.10 ± 0.08 | 0.52 |
| Longissimus thoracis area, cm$^2$ | 74.30 ± 1.11 | 73.07 ± 0.97 | 72.71 ± 1.41 | 0.46 |
| *Average measurements[x]* | | | | |
| Body weight, kg | 416.9 ± 2.44 | 415.04 ± 2.31 | 413.92 ± 2.49 | 0.28 |
| Ultrasound backfat | 4.82 ± 0.16 | 5.05 ± 0.14 | 5.38 ± 0.21 | 0.04 |
| Ultrasound marbling score | 4.34 ± 0.06 | 4.35 ± 0.06 | 4.35 ± 0.07 | 0.94 |
| Longissimus thoracis area, cm$^2$ | 68.01 ± 0.46 | 68.10 ± 0.40 | 68.46 ± 0.58 | 0.74 |
| *Predicted @ 500 kg* | | | | |
| Ultrasound backfat | 6.54 ± 0.31 | 6.47 ± 0.26 | 7.22 ± 0.38 | 0.19 |
| Ultrasound marbling score | 4.89 ± 0.08 | 4.87 ± 0.07 | 5.05 ± 0.10 | 0.33 |
| Longissimus thoracis area, cm$^2$ | 71.49 ± 0.79 | 71.61 ± 0.68 | 71.41 ± 0.99 | 0.98 |
| *Carcass data* | | | | |
| Number of animals | 36 | 47 | 26 | |
| Slaughter weight, kg | 510.23 ± 8.85 | 489.62 ± 7.67 | 479.87 ± 11.21 | 0.02 |
| Carcass weight, kg | 306.99 ± 5.28 | 286.81 ± 4.63 | 287.17 ± 6.27 | 0.01 |
| Grade Fat, mm | 8.98 ± 0.56 | 8.19 ± 0.48 | 9.55 ± 0.65 | 0.23 |
| Ave. Backfat, mm | 10.51 ± 0.58 | 9.72 ± 0.50 | 10.99 ± 0.68 | 0.29 |
| Carcass marbling score | 2.37 ± 0.09 | 2.21 ± 0.08 | 2.44 ± 0.11 | 0.20 |
| L. thoracis area, cm$^2$ | 76.12 ± 2.73 | 75.18 ± 2.60 | 74.63 ± 2.54 | 0.67 |
| Lean meat yield, % | 58.07 ± 0.54 | 58.76 ± 0.46 | 57.63 ± 0.63 | 0.32 |

[z]EXON2-FB polymorphism is a C/T substitution located at position 305 of exon 2 of the bovine leptin gene according to SEQ ID NO: 5 (Gen bank accession no. AY138588 - see also Buchanan et al., 2002).
[y]P value = probability of differences among different marker genotypes.
[x]Average of five measurements taken between January 10 and May 01 at approximately monthly intervals Final body weight (additive effect, a=30.32±9.9 kg) and carcass weight (additive effect, a=19.82±5.78 kg), P=0.01) were lower (P<0.05) for TT animals of EXON2-FB compared to the CC animals. No significant associations were detected between EXON2-FB and the other traits studied. Measures of carcass fatness were generally higher and measures of carcass lean meat yield and longissimus muscle area were lower for TT animals compared to CC animals of EXON2-FB, though no statistical significance was detected. Chi-square analysis of the carcass grades (A, AA, and AAA) among genotypes of EXON2-FB showed no significant associations between quality grade and genotypes ($\chi^2$=0.95, P=0.62) (Table 11).

Three polymorphisms in the bovine leptin promoter are associated with growth rate, body weight, feed intake, feeding behavior and ultrasound merit. Though some differences in carcass fatness were detected, these were not statistically significant, possibly due to the removal of some extreme animals based on residual feed intake (correlation between RFI and backfat is about r=0.25) for some metabolic studies. In addition, one of the markers, UASMS2 is associated with serum leptin levels in cattle. The frequency of this SNP was very low in both the experimental population and the five commercial lines of cattle studied.

TABLE 11

Distribution of carcass quality grades among genotypes of the different markers

| | | Carcass quality grades | | | |
|---|---|---|---|---|---|
| Polymorphism | Genotype | A | AA | AAA | Chi-square test |
| UASMS1-3 | CC-CC | 5 | 10 | 7 | $\chi^2$ = 1.37, P = 0.50 |
| | CT-CG | 13 | 27 | 9 | |
| | TT-GG | 7 | 23 | 8 | |
| UASMS2 | CC | 20 | 40 | 16 | $\chi^2$ = 1.14, P = 0.56 |
| | CT | 4 | 18 | 7 | |
| | TT | 1 | 2 | 1 | |
| EXON2-FB | CC | 6 | 22 | 8 | $\chi^2$ = 0.95, P = 0.62 |
| | CT | 14 | 25 | 8 | |
| | TT | 5 | 13 | 8 | |

Unlike the UASMS1 and UASMS3 polymorphisms, the UASMS2 and UASMS3 polymorphisms are not linked. This can be seen in Table 12 which illustrates the linkage disequilibrium between the UASMS2 and UASMS3 polymorphisms.

TABLE 12

Test of linkage disequilibrium using percentage deviations of observed from expected pairwise genotype combinations of UASMS3 and UASMS2

| UASMS2 genotypes | Frequency | UASMS3 genotypes | | |
|---|---|---|---|---|
| | | CC 0.18 | CG 0.46 | GG 0.36 |
| CC | 0.63 | 6.96 | −0.68 | −6.58 |
| CT | 0.32 | −5.76 | 2.58 | 3.58 |
| TT | 0.05 | −2.30 | −0.90 | 3.20 |

The invention is further described by the following numbered paragraphs:

1. A method for sub grouping animals according to genotype wherein the animals of each sub-group have a similar polymorphism in the leptin gene comprising:
    (a) determining the genotype of each animal to be sub-grouped by determining the presence of a single nucleotide polymorphism in the leptin gene, wherein the polymorphism is selected from the group consisting of UASMS1, UASMS2, UASMS3 and EXON2-FB, and
    (b) segregating individual animals into sub-groups wherein each animal in a subgroup has a similar polymorphism in the leptin gene.
2. The method of paragraph 1 wherein the animal is a bovine.
3. The method of paragraph 2 wherein the leptin gene is the bovine leptin gene.
4. A method for sub grouping animals according to genotype wherein the animals of each sub-group have a similar genotype in the leptin gene comprising:
    (a) determining the genotype of each animal to be sub-grouped by determining the presence of the UASMS1, UASMS2, UASMS3 or EXON2-FB, single nucleotide polymorphism(s) in the leptin gene,
    (b) segregating individual animals into sub-groups depending on whether the animals have, or do not have, the UASMS1, UASMS2, and/or UASMS3 single nucleotide polymorphism(s) in the leptin gene.
5. The method of paragraph 4 wherein the animal is a bovine.
6. The method of paragraph 5 wherein the leptin gene is the bovine leptin gene.
7. A method for sub grouping animals according to genotype wherein the animals of each sub-group have a similar genotype in the promoter region of the leptin gene comprising:
    (a) determining the genotype of each animal to be sub-grouped by determining the presence of the UASMS1 single nucleotide polymorphism in the promoter region of the leptin gene, and
    (b) segregating individual animals into sub-groups depending on whether the animals have, or do not have, the UASMS1 single nucleotide polymorphism in the promoter region of the leptin gene.
8. The method of paragraph 7 wherein the animal is a bovine.
9. The method of paragraph 8 wherein the leptin gene is the bovine leptin gene.
10. A method for sub grouping animals according to genotype wherein the animals of each sub-group have a similar genotype in the promoter region of the leptin gene comprising:
    (a) determining the genotype of each animal to be sub-grouped by determining the presence of the UASMS2 single nucleotide polymorphism in the promoter region of the leptin gene, and
    (b) segregating individual animals into sub-groups depending on whether the animals have, or do not have, the UASMS2 single nucleotide polymorphism in the promoter region of the leptin gene.
11. The method of paragraph 10 wherein the animal is a bovine.
12. The method of paragraph 11 wherein the leptin gene is the bovine leptin gene.
13. A method for sub grouping animals according to genotype wherein the animals of each sub-group have a similar genotype in the promoter region of the leptin gene comprising:
    (a) determining the genotype of each animal to be sub-grouped by determining the presence of the UASMS3 single nucleotide polymorphism in the promoter region of the leptin gene, and
    (b) segregating individual animals into sub-groups depending on whether the animals have, or do not have, the UASMS3 single nucleotide polymorphism in the promoter region of the leptin gene.
14. The method of paragraph 13 wherein the animal is a bovine.
15. The method of paragraph 14 wherein the leptin gene is the bovine leptin gene.
16. A method for sub grouping animals according to genotype wherein the animals of each sub-group have a similar genotype in exon 2 of the leptin gene comprising:
    (a) determining the genotype of each animal to be sub-grouped by determining the presence of the exon2-FB single nucleotide polymorphism in exon 2 of the leptin gene, and
    (b) segregating individual animals into sub-groups depending on whether the animals have, or do not have, the exon2-FB single nucleotide polymorphism in the promoter region of the leptin gene.
17. The method of paragraph 16 wherein the animal is a bovine.
18. The method of paragraph 17 wherein the leptin gene is the bovine leptin gene.
19. A method for identifying an animal having a desirable phenotype relating to certain feed intake, growth rate, body weight, carcass merit and composition, and milk yield, as compared to the general population of animals of that species, comprising determining the presence of a single nucleotide polymorphism in the leptin gene of the animal, wherein the polymorphism is selected from the group consisting of UASMS1, UASMS2, UASMS3, and EXON2-FB, wherein the presence of either the UASMS1, UASMS2, UASMS3 or EXON2-FB single nucleotide polymorphism is indicative of a desirable phenotype relating to certain feed intake, growth rate, body weight, carcass merit and composition, and milk yield.
20. The method of paragraph 1 wherein the animal is a bovine.
21. The method of paragraph 2 wherein the leptin gene is the bovine leptin gene.
22. A method for identifying an animal having a desirable phenotype relating to certain feed intake, growth rate, body weight, carcass merit and composition, and milk yield, as compared to the general population of animals of that species, comprising determining the presence of the UASMS1 single nucleotide polymorphism in the promoter region of the leptin gene of the animal, wherein the presence the UASMS1, single nucleotide polymorphism is indicative of a desirable phenotype relating to certain feed intake, growth rate, body weight, carcass merit and composition, and milk yield.
23. The method of paragraph 22 wherein the animal is a bovine.
24. The method of paragraph 2 wherein the leptin gene is the bovine leptin gene.

25. A method for identifying an animal having a desirable phenotype relating to certain feed intake, growth rate, body weight, carcass merit and composition, and milk yield, as compared to the general population of animals of that species, comprising determining the presence of the UASMS2 single nucleotide polymorphism in the promoter region of the leptin gene of the animal, wherein the presence the UASMS2, single nucleotide polymorphism is indicative of a desirable phenotype relating to certain feed intake, growth rate, body weight, carcass merit and composition, and milk yield.

26. The method of paragraph 25 wherein the animal is a bovine.

27. The method of paragraph 26 wherein the leptin gene is the bovine leptin gene.

28. A method for identifying an animal having a desirable phenotype relating to certain feed intake, growth rate, body weight, carcass merit and composition, and milk yield, as compared to the general population of animals of that species, comprising determining the presence of the UASMS3 single nucleotide polymorphism in the promoter region of the leptin gene of the animal, wherein the presence the UASMS3, single nucleotide polymorphism is indicative of a desirable phenotype relating to certain feed intake, growth rate, body weight, carcass merit and composition, and milk yield.

29. The method of paragraph 28 wherein the animal is a bovine.

30. The method of paragraph 29 wherein the leptin gene is the bovine leptin gene.

31. A method for identifying an animal having a desirable phenotype relating to certain feed intake, growth rate, body weight, carcass merit and composition, and milk yield, as compared to the general population of animals of that species, comprising determining the presence of the EXON2-FB single nucleotide polymorphism in the leptin gene of the animal, wherein the presence the EXON2-FB single nucleotide polymorphism is indicative of a desirable phenotype relating to certain feed intake, growth rate, body weight, carcass merit and composition, and milk yield.

32. The method of paragraph 31 wherein the animal is a bovine.

33. The method of paragraph 32 wherein the leptin gene is the bovine leptin gene.

34. An isolated oligonucleotide probe for detecting the UASMS1 ob gene polymorphism, wherein the probe comprises at least 10 contiguous nucleotides of SEQ ID NO: 2, and wherein the 10 contiguous nucleotides span nucleotide position 207 of SEQ ID NO: 2.

35. An isolated oligonucleotide probe for detecting the T-containing allele at nucleotide position 207 of the ob gene promoter, wherein the probe comprises at least 10 contiguous nucleotides of SEQ ID NO: 2, and wherein the 10 contiguous nucleotides span the T nucleotide at position 207 of SEQ ID NO: 2.

36. An isolated oligonucleotide probe for detecting the C-containing allele at nucleotide position 207 of the ob gene promoter, wherein the probe comprises at least 10 contiguous nucleotides of SEQ ID NO: 1, and wherein the 10 contiguous nucleotides span the C nucleotide at position 207 of SEQ ID NO: 1.

37. An isolated oligonucleotide probe for detecting the T-containing allele at nucleotide position 207 of the ob gene promoter, wherein the probe has the sequence of SEQ ID NO: 9.

38. An isolated oligonucleotide probe for detecting the C-containing allele at nucleotide position 207 of the ob gene promoter, wherein the probe has the sequence of SEQ ID NO: 10.

39. An isolated oligonucleotide probe for detecting the UASMS2 ob gene polymorphism, wherein the probe comprises at least 10 contiguous nucleotides of SEQ ID NO:3, and wherein the 10 contiguous nucleotides span nucleotide position 528 of SEQ ID NO: 2.

40. An isolated oligonucleotide probe for detecting the T-containing allele at nucleotide position 528 of the ob gene promoter, wherein the probe comprises at least 10 contiguous nucleotides of SEQ ID NO: 3, and wherein the 10 contiguous nucleotides span the T nucleotide at position 528 of SEQ ID NO: 3.

41. An isolated oligonucleotide probe for detecting the C-containing allele at nucleotide position 528 of the ob gene promoter, wherein the probe comprises at least 10 contiguous nucleotides of SEQ ID NO: 1, and wherein the 10 contiguous nucleotides span the C nucleotide at position 528 of SEQ ID NO: 1.

42. An isolated oligonucleotide probe for detecting the T-containing allele at nucleotide position 528 of the ob gene promoter, wherein the probe has the sequence of SEQ ID NO: 14.

43. An isolated oligonucleotide probe for detecting the C-containing allele at nucleotide position 528 of the ob gene promoter, wherein the probe has the sequence of SEQ ID NO: 13.

44. An isolated oligonucleotide probe for detecting the UASMS3 ob gene polymorphism, wherein the probe comprises at least 10 contiguous nucleotides of SEQ ID NO:4, and wherein the 10 contiguous nucleotides span nucleotide position 1759 of SEQ ID NO: 4.

45. An isolated oligonucleotide probe for detecting the G-containing allele at nucleotide position 1759 of the ob gene promoter, wherein the probe comprises at least 10 contiguous nucleotides of SEQ ID NO: 4, and wherein the 10 contiguous nucleotides span the G nucleotide at position 1759 of SEQ ID NO: 4.

46. An isolated oligonucleotide probe for detecting the C-containing allele at nucleotide position 1759 of the ob gene promoter, wherein the probe comprises at least 10 contiguous nucleotides of SEQ ID NO: 1, and wherein the 10 contiguous nucleotides span the C nucleotide at position 1759 of SEQ ID NO: 1.

47. An isolated oligonucleotide probe for detecting the G-containing allele at nucleotide position 1759 of the ob gene promoter, wherein the probe has the sequence of SEQ ID NO: 17.

48. An isolated oligonucleotide probe for detecting the C-containing allele at nucleotide position 1759 of the ob gene promoter, wherein the probe has the sequence of SEQ ID NO: 18.

49. An isolated oligonucleotide probe for detecting the EXON2-FB ob gene polymorphism, wherein the probe comprises at least 10 contiguous nucleotides of SEQ ID NO:6, and wherein the 10 contiguous nucleotides span nucleotide position 305 of SEQ ID NO:6.

50. An isolated oligonucleotide probe for detecting the C-containing allele at nucleotide position 305 of exon 2 of the ob gene, wherein the probe comprises at least 10 contiguous nucleotides of SEQ ID NO: 5, and wherein the 10 contiguous nucleotides span the C nucleotide at position 305 of SEQ ID NO: 5.

51. An isolated oligonucleotide probe for detecting the T-containing allele at nucleotide position 305 of exon 2 of the ob gene, wherein the probe comprises at least 10 contiguous nucleotides of SEQ ID NO: 6, and wherein the 10 contiguous nucleotides span the T nucleotide at position 305 of SEQ ID NO: 6.
52. An isolated oligonucleotide probe for detecting the C-containing allele at nucleotide position 305 of exon 2 of ob gene, wherein the probe has the sequence of SEQ ID NO: 22.
53. An isolated oligonucleotide probe for detecting the T-containing allele at nucleotide position 305 of exon 2 of the ob gene, wherein the probe has the sequence of SEQ ID NO: 21.
54. A composition for the detection of an ob gene polymorphism, comprising at least one oligonucleotide probe according to any one of paragraphs 34 to 53.
55. An isolated oligonucleotide probe according to any one of claims 34 to 53 wherein the oligonucleotide is labeled with a detectable moiety.
56. A composition for the detection of an ob gene polymorphism, comprising at least one oligonucleotide probe according to paragraph 55.
57. An isolated oligonucleotide probe according to paragraph 55 wherein the detectable moiety is selected from the group consisting of a radiolabel $^3$H, $^{125}$I, $^{35}$S, $^{14}$C, $^{32}$P, a detectable enzyme, horse radish peroxidase (HRP), alkaline phosphatase, a fluorescent dye, fluorescein isothiocyanate, Texas red, rhodamine, Cy3, Cy5, Bodipy, Bodipy Far Red, Lucifer Yellow, Bodipy 630/650-X, Bodipy R6G-X, 5-CR 6G, a colorimetric label, colloidal gold digoxigenin-dUTP, or biotin.
58. A composition for the detection of an ob gene polymorphism, comprising at least one oligonucleotide probe according to paragraph 57.
59. An isolated oligonucleotide probe according to paragraph 55 wherein the detectable moiety is a fluorescent component generating a fluorescent signal.
60. A composition for the detection of an ob gene polymorphism, comprising at least one oligonucleotide probe according to paragraph 59.
61. An isolated oligonucleotide according to any one of paragraphs 34 to 53 wherein the oligonucleotide is immobilized on a solid support.
62. A primer pair for enzymatic amplification of a fragment of the ob gene promoter spanning the location of the UASMS1 polymorphism, comprising a pair of oligonucleotides which complement and specifically anneal to the ob gene promoter, wherein the first member of the primer pair anneals to the ob gene promoter at a location upstream (5') of nucleotide position 207, and the second member of the primer pair anneals to the ob gene promoter at a location downstream (3') of nucleotide position 207.
63. A primer pair for enzymatic amplification of a fragment of the ob gene promoter spanning the location of the UASMS1 polymorphism, comprising a forward primer having the sequence of SEQ ID NO: 7, and a reverse primer having the sequence of SEQ ID NO: 8.
64. An isolated primer useful in the enzymatic amplification of a fragment of the ob gene promoter spanning the location of the UASMS1 polymorphism, wherein the primer has the sequence of SEQ ID NO: 7.
65. An isolated primer useful in the enzymatic amplification of a fragment of the ob gene promoter spanning the location of the UASMS1 polymorphism, wherein the primer has the sequence of SEQ ID NO: 8.
66. A primer pair for enzymatic amplification of a fragment of the ob gene promoter spanning the location of the UASMS2 polymorphism, comprising a pair of oligonucleotides which complement and specifically anneal to the ob gene promoter, wherein the first member of the primer pair anneals to the ob gene promoter at a location upstream (5') of nucleotide position 528, and the second member of the primer pair anneals to the ob gene promoter at a location downstream (3') of nucleotide position 528.
67. A primer pair for enzymatic amplification of a fragment of the ob gene promoter spanning the location of the UASMS2 polymorphism, comprising a forward primer having the sequence of SEQ ID NO: 11, and a reverse primer having the sequence of SEQ ID NO: 12.
68. An isolated primer useful in the enzymatic amplification of a fragment of the ob gene promoter spanning the location of the UASMS2 polymorphism, wherein the primer has the sequence of SEQ ID NO: 11.
69. An isolated primer useful in the enzymatic amplification of a fragment of the ob gene promoter spanning the location of the UASMS2 polymorphism, wherein the primer has the sequence of SEQ ID NO: 12.
70. A primer pair for enzymatic amplification of a fragment of the ob gene promoter spanning the location of the UASMS3 polymorphism, comprising a pair of oligonucleotides which complement and specifically anneal to the ob gene promoter, wherein the first member of the primer pair anneals to the ob gene promoter at a location upstream (5') of nucleotide position 1759, and the second member of the primer pair anneals to the ob gene promoter at a location downstream (3') of nucleotide position 1759.
71. A primer pair for enzymatic amplification of a fragment of the ob gene promoter spanning the location of the UASMS3 polymorphism, comprising a forward primer having the sequence of SEQ ID NO: 15, and a reverse primer having the sequence of SEQ ID NO: 16.
72. An isolated primer useful in the enzymatic amplification of a fragment of the ob gene promoter spanning the location of the UASMS3 polymorphism, wherein the primer has the sequence of SEQ ID NO: 15.
73. An isolated primer useful in the enzymatic amplification of a fragment of the ob gene promoter spanning the location of the UASMS3 polymorphism, wherein the primer has the sequence of SEQ ID NO: 16.
74. A primer pair for enzymatic amplification of a fragment of the ob gene spanning the location of the EXON2-FB polymorphism, comprising a pair of oligonucleotides which complement and specifically anneal to the ob gene, wherein the first member of the primer pair anneals to the ob gene at a location upstream (5') of nucleotide position 305 of exon 2, and the second member of the primer pair anneals to the ob gene at a location downstream (3') of nucleotide position 305 of exon 2.
75. A primer pair for enzymatic amplification of a fragment of the ob gene spanning the location of the EXON2-FB polymorphism, comprising a forward primer having the sequence of SEQ ID NO: 19, and a reverse primer having the sequence of SEQ ID NO: 20.
76. An isolated primer useful in the enzymatic amplification of a fragment of the ob gene spanning the location of the EXON2-FB polymorphism, wherein the primer has the sequence of SEQ ID NO: 19.
77. An isolated primer useful in the enzymatic amplification of a fragment of the ob gene spanning the location of the EXON2-FB polymorphism, wherein the primer has the sequence of SEQ ID NO: 20.

78. A method of determining the genotype of an animal at the polymorphic UASMS1 locus of the ob gene comprising
   a) obtaining a DNA sample from the animal
   b) contacting the DNA sample with the oligonucleotide primer pair of SEQ ID NO:7 and SEQ ID NO:8 under conditions suitable for permitting hybridization of the oligonucleotide primers to the DNA sample,
   c) enzymatically amplifying a specific region of the ob gene using the primer pair of SEQ ID NO:7 and SEQ ID NO:8 to form nucleic acid amplification products,
   d) contacting the amplification products from step c) with labeled allele-specific probes comprising of SEQ ID NO:9 and SEQ ID NO:10, labeled with a detectable moiety, under conditions suitable for permitting hybridization of the labeled allele-specific probes to the amplification products, and
   e) detecting the presence of the amplification products by detecting the detectable moiety of the labeled allele-specific probes hybridized to the amplification products.

79. A method of determining the genotype of an animal at the polymorphic UASMS2 locus of the ob gene comprising
   a) obtaining a DNA sample from the animal
   b) contacting the DNA sample with the oligonucleotide primer pair of SEQ ID NO:11 and SEQ ID NO:12 under conditions suitable for permitting hybridization of the oligonucleotide primers to the DNA sample,
   c) enzymatically amplifying a specific region of the ob gene using the primer pair of SEQ ID NO:11 and SEQ ID NO:12 to form nucleic acid amplification products,
   d) contacting the amplification products from step c) with labeled allele-specific probes comprising of SEQ ID NO:13 and SEQ ID NO:14, labeled with a detectable moiety, under conditions suitable for permitting hybridization of the labeled allele-specific probes to the amplification products, and
   e) detecting the presence of the amplification products by detecting the detectable moiety of the labeled allele-specific probes hybridized to the amplification products.

78. A method of determining the genotype of an animal at the polymorphic UASMS3 locus of the ob gene comprising
   a) obtaining a DNA sample from the animal
   b) contacting the DNA sample with the oligonucleotide primer pair of SEQ ID NO:15 and SEQ ID NO:16 under conditions suitable for permitting hybridization of the oligonucleotide primers to the DNA sample,
   c) enzymatically amplifying a specific region of the ob gene using the primer pair of SEQ ID NO:15 and SEQ ID NO:16 to form nucleic acid amplification products,
   d) contacting the amplification products from step c) with labeled allele-specific probes comprising of SEQ ID NO:17 and SEQ ID NO:18, labeled with a detectable moiety, under conditions suitable for permitting hybridization of the labeled allele-specific probes to the amplification products, and
   e) detecting the presence of the amplification products by detecting the detectable moiety of the labeled allele-specific probes hybridized to the amplification products.

78. A method of determining the genotype of an animal at the polymorphic EXON2-FB locus of the ob gene comprising
   a) obtaining a DNA sample from the animal
   b) contacting the DNA sample with the oligonucleotide primer pair of SEQ ID NO:19 and SEQ ID NO:20 under conditions suitable for permitting hybridization of the oligonucleotide primers to the DNA sample,
   c) enzymatically amplifying a specific region of the ob gene using the primer pair of SEQ ID NO:19 and SEQ ID NO:20 to form nucleic acid amplification products,
   d) contacting the amplification products from step c) with labeled allele-specific probes comprising of SEQ ID NO:21 and SEQ ID NO:22, labeled with a detectable moiety, under conditions suitable for permitting hybridization of the labeled allele-specific probes to the amplification products, and
   e) detecting the presence of the amplification products by detecting the detectable moiety of the labeled allele-specific probes hybridized to the amplification products.

What is claimed is:

1. A method for identifying a bovine animal as having a particular daily dry matter intake, body weight, slaughter weight, or carcass weight phenotype, said method comprising:
    (a) obtaining a biological sample from a bovine, said sample comprising nucleic acids from said bovine;
    (b) detecting in said nucleic acids the nucleotide content at both alleles of the UASMS1 or UASMS3 polymorphic position in the leptin gene to determine the UASMS1 or UASMS3 genotype of the bovine, wherein the UASMS1 polymorphic position is either a C or a T at position 207 of SEQ ID NO: 1 and the UASMS3 polymorphic position is either a C or a G at position 1759 of SEQ ID NO: 1; and
    (c) correlating the UASMS1 or UASMS3 genotype with the daily dry matter intake, body weight, slaughter weight, or carcass weight phenotype of the bovine, wherein:
        (i) the presence of a CC UASMS1 genotype or a CC UASMS3 genotype is indicative of lower daily dry matter intake, body weight, slaughter weight, or carcass weight phenotype;
        (ii) the presence of a TT UASMS1 genotype or a GG UASMS3 genotype is indicative of higher daily dry matter intake, body weight, slaughter weight, or carcass weight phenotype; and
        (iii) the presence of a heterozygous CT UASMS1 genotype or a CG UASMS3 genotype is indicative of a daily dry matter intake, body weight, slaughter weight, or carcass weight phenotype that is intermediate to the level of said phenotypes in animals having a CC UASMS1 genotype, a CC UASMS3 genotype, a TT UASMS1 genotype or a GG UASMS3.

2. A method for selectively breeding bovine animals that have particular daily dry matter intake, body weight, slaughter weight, or carcass weight phenotypes, comprising:
    (a) extracting DNA from a tissue or blood sample of bovine animals;
    (b) amplifying said DNA with:
        (i) a first primer that anneals to the leptin gene promoter at a location upstream of nucleotide position 207 of SEQ ID NO: 1; and a second primer that anneals to the leptin gene promoter at a location downstream of nucleotide position 207 of SEQ ID NO: 1;
        (ii) a first primer that anneals to the leptin gene promoter at a location upstream of nucleotide position 1759 of SEQ ID NO: 1; and a second primer that anneals to the leptin gene promoter at a location downstream of nucleotide position 1759 of SEQ ID NO: 1;
        (iii) a first primer comprising SEQ ID NO: 7; and a second primer comprising SEQ ID NO: 8; or
        (iv) a first primer comprising SEQ ID NO: 15; and a second primer comprising SEQ ID NO: 16;
    (c) determining the genotypes of said subject bovine animals at polymorphic position UASMS1 or UASMS3, wherein the UASMS1 polymorphic position is either a C or a T at position 207 of SEQ ID NO: 1 and the UASMS3 polymorphic position is either a C or a G at position 1759 of SEQ ID NO: 1;
    (d) grouping individual animals into sub-groups wherein each animal in a sub-group has the same genotype at the position of the UASMS1 or UASMS3 polymorphism; and
    (e) selectively breeding animals from particular sub-groups.

* * * * *

SEQUENCE LISTING

```
<160> NUMBER OF SEQ ID NOS: 22

<210> SEQ ID NO 1
<211> LENGTH: 3052
<212> TYPE: DNA
<213> ORGANISM: Bos taurus

<400> SEQUENCE: 1
gaattcaaca attctattta tcaagaaatc tcccacaaat atactcacac tgtgctccaa      60
taagtacttt tgagtctatt aattaacaac attatgtatc taacattatg gttagattga     120
ttatggtgca tctgtgaaat gaaacatacg ctgactctaa aatgattggc acaatcctgt     180
gtattggtaa gaaattgtat tctagatata ctaggtgaaa gaagtgagat taataatggt     240
taaaattggg caatggtaca tggacatttg taatgccatt tttccttata agtgtattgt     300
ggagatttaa atttttccaa aaaaaaaaat gtggaggcag ggggcaagaa cattagtgtg     360
aataatatga cattatttaa atgcccttaa atatatattt tttaattaat ttatttattt     420
tttctatgct gggtcttcat tgcaatgtgc aagcttctca ctgtggcagc ttctcctgtt     480
gtggagcata ggctccaggt gcccagggac tcagcggttg caacacacag gctctagagc     540
ttgggctcgg gagccgtgtc acacggcctt tgttgctccc agcatgtgga atcttcctca     600
```

```
accagggacc gatcccgcgt ccctgcactg gcaggcggat tctcatccac tgtaccacca      660
aggaaggcct gcacactttt tttttttaagg aaatggatat atgaaggaca gaaaaagaat    720
atccatggaa ggatacacca taaactgaga agaacaacta cttctaggga aaaaaggact    780
ggggagagac tgagttttca tatctttgtt cctttttgaat tttaagaaaa ataatacatt    840
attctaacac aacattgtaa agcaattata cttcaataaa aaattaaaag taaaaatact    900
ttattatata ataatatata attataatat aatataaaca ttcagttcag ttcagttcac    960
ttcagtcgct cagtcgtgtc cgactctttt cgaccccatg aatcgcagca caccaggcct   1020
ccctgtccat caccaactcc cggagttcac ccagactcat agtaatatat aataatttat   1080
tttaaaataa ttattaatca acacgaaatg taaaaaatag gtaggtgatg ggtagatagg   1140
cagacgggca gtccacacac tcacatgtgg tctcaagtgc tacttggtgt tcaggcaata   1200
actctggtcc caatctgacc tctgacccct aaaaaggtga tggtaagaca agtaacctga   1260
ggctgccagg gccctgcct atgagctaag actctgctta gaaccaagtt acaaagatgt    1320
tgcagacaag aaaaatttgg tcgtagtgga tgctactgcc tctatttgaa aacaacaca    1380 aacatttccg ggggggggggg gaggcggaga ggaggaaaga ttttcttcaa aatgtaattt   1440
cattgtagac acttctttaa aagaaacatt tctttatttg acagttccag gccttagttt    1500
cagcaggcag gatgtttagt cgcagcatga gaactcttag ctgcggcatg cgggacccag   1560
ttcagttccc tgaccagata tcgaacctgg ggccctgca tttggaagca gggagtctta   1620
gccactggac caccagggaa gtcccctgta gatgttttta tgaaaagcag aaaagcacaa   1680
agaagagctt aaagattcct gatcctactc ccaatagtga taatgtatat tttggtgtga   1740
gagtgtgtgt attgattgga atgtgtgtga tcagaaaaca cataccatt tataatccgt    1800 tctttccagc tcacaaaata aagttatttt cctacatcat taaatattac tttacaacat   1860 aattttttaat gtgtgcatat tgctgctatg tgattttcaa taacttacta atttcctatg   1920
ctgaacattt agttgttgtc caaccttttt agtggccatg taattataaa tcatggtcaa   1980
tgctaacaat ttctgacctc acaaacatat agtacaatat ccttccttc ttcaatagat    2040 aattattaaa agcaaaacaa ccaggctcaa acaaagcaat tataaaatat ctttaaaaag   2100
acattgggta aaattcaaat gcagactagc tcatgatgtt aaagaattac tcttgtgtgg   2160
taatggtctt gtgatagaga tagaaatgct tccttatttt tcagataaac acttaagtat   2220
ttaaggatga aacgccctga tgtttgtaat ttgctttaga atattttagc caaaagaatt   2280
aatgatgcaa atatgcaaaa agagtacgtt aaacctaaat ttgcgatttt catttaaaaa    2340
tatatcttaa aaatgaaaat cttcgtgcaa cgcacggggc tatcaatgtg ggatacagat   2400
gtgaacaaaa cggacccgtg tgggactcgg cggagcacac agattttgcg ggagcacgtt   2460
cccgttagga agtctctgat gcaatacgac cggtgccctt caggacctgt gagactgact   2520
ttccttaccc ctccacacca tcatcaaggc aggtgtgatt ttccaggcca ggcctacggc   2580
cgggtttccc cggggggccca gagccgtcgg gtcttgccgc ccagcggagc tggctgctcc   2640
ggcctcactg tcggggcgcc accgcccca gccggctcag aggaacccct caccgccacc    2700
ctgtcccagg cggcctttcc ccgaggcccg agggtcagat cctggggcca cctcgaggat   2760
ttctcacacc tgcccagcca ccccagctt ttcaggtgat accggagggt gggcgtgggg    2820
ctcctggcgc atccgagtcc ctccctggag tccccgaccg cggccgcccg gcccgacgct   2880
gccccgccgc cccgcagggc gggagccggc gctgcgggtg cgccccggcc agccgggcag   2940
ttgcgcaagt tgtgcttcgg cggctataag aggggcgggc aggcatggag ccccggaggg   3000
```

```
atcgaggaat cgcggcgcca gcagcggcga ggtaagtgcc cggctctctc ct         3052

<210> SEQ ID NO 2
<211> LENGTH: 3052
<212> TYPE: DNA
<213> ORGANISM: Bos taurus

<400> SEQUENCE: 2
gaattcaaca attctatttta tcaagaaatc tcccacaaat atactcacac tgtgctccaa   60
taagtacttt tgagtctatt aattaacaac attatgtatc taacattatg gttagattga  120
ttatggtgca tctgtgaaat gaaacatacg ctgactctaa aatgattggc acaatcctgt  180
gtattggtaa gaaattgtat tctagacata ctaggtgaaa gaagtgagat taataatggt  240
taaaattggg caatggtaca tggacatttg taatgccatt tttccttata agtgtattgt  300
ggagatttaa attttttccaa aaaaaaaaat gtggaggcag gggcaagaa cattagtgtg  360 aataatatga cattattttaa atgccccttaa atatatattt tttaattaat ttatttattt  420
tttctatgct gggtcttcat tgcaatgtgc aagcttctca ctgtggcagc ttctcctgtt  480
gtggagcata ggctccaggt gcccagggac tcagcggttg caacacacag gctctagagc  540
ttgggctcgg gagccgtgtc acacggcctt tgttgctccc agcatgtgga atcttcctca  600
accagggacc gatcccgcgt ccctgcactg gcaggcggat tctcatccac tgtaccacca  660
aggaaggcct gcacactttt tttttaagg aaatggatat atgaaggaca gaaaagaat  720 atccatggaa ggatacacca taaactgaga agaacaacta cttctaggga aaaaaggact  780
ggggagagac tgagttttca tatctttgtt ccttttgaat tttaagaaaa ataatacatt  840
attctaacac aacattgtaa agcaattata cttcaataaa aaattaaaag taaaaatact  900
ttattatata ataatatata attataatat aatataaaca ttcagttcag ttcagttcac  960
ttcagtcgct cagtcgtgtc cgactctttt cgaccccatg aatcgcagca caccaggcct 1020
ccctgtccat caccaactcc cggagttcac ccagactcat agtaatatat aataatttat 1080
tttaaaataa ttattaatca acacgaaatg taaaaaatag gtaggtgatg ggtagataagg 1140 cagacgggca gtccacacac tcacatgtgg tctcaagtgc tacttggtgt tcaggcaata 1200
actctggtcc caatctgacc tctgaccctt aaaaggtga tggtaagaca agtaacctga 1260
ggctgccagg gcccctgcct atgagctaag actctgctta gaaccaagtt acaaagatgt 1320
tgcagacaag aaaaatttgg tcgtagtgga tgctactgcc tctattttgaa aaacaacaca 1380 aacatttccg gggggggggg gaggcggaga ggaggaaaga ttttcttcaa aatgtaattt 1440
cattgtagac acttctttaa aagaaacatt tctttatttg acagttccag gccttagttt 1500
cagcaggcag gatgtttagt cgcagcatga gaactcttag ctgcggcatg cgggacccag 1560
ttcagttccc tgaccagata tcgaacctgg ggccccctgca tttggaagca gggagtctta 1620
gccactggac caccagggaa gtcccctgta gatgttttta tgaaaagcag aaaagcacaa 1680
agaagagctt aaagattcct gatcctactc ccaatagtga taatgtatat tttggtgtga 1740
gagtgtgtgt attgattgga atgtgtgtga tcagaaaaca cataccatt tataatccgt 1800 tctttccagc tcacaaaata aagttatttt cctacatcat taaatattac tttacaacat 1860 aattttaat gtgtgcatat tgctgctatg tgattttcaa taacttacta atttcctatg 1920
ctgaacattt agttgttgtc caaccttttt agtggccatg taattataaa tcatggtcaa 1980
tgctaacaat ttctgacctc acaaacatat agtacaatat ccttcctttc ttcaatagat 2040
aattattaaa agcaaaacaa ccaggctcaa acaaagcaat tataaaatat ctttaaaaag 2100
```

```
acattgggta aaattcaaat gcagactagc tcatgatgtt aaagaattac tcttgtgtgg      2160
taatggtctt gtgatagaga tagaaatgct tccttatttt tcagataaac acttaagtat      2220
ttaaggatga aacgccctga tgtttgtaat ttgctttaga atattttagc caaaagaatt      2280
aatgatgcaa atatgcaaaa agagtacgtt aaacctaaat ttgcgatttt catttaaaaa      2340
tatatcttaa aaatgaaaat cttcgtgcaa cgcacggggc tatcaatgtg ggatacagat      2400
gtgaacaaaa cggacccgtg tgggactcgg cggagcacac agattttgcg ggagcacgtt      2460
cccgttagga agtctctgat gcaatacgac cggtgccctt caggacctgt gagactgact      2520
ttccttaccc ctccacacca tcatcaaggc aggtgtgatt ttccaggcca ggcctacggc      2580
cgggtttccc cggggggccca gagccgtcgg gtcttgccgc ccagcggagc tggctgctcc      2640
ggcctcactg tcggggcgcc accgccccca gccggctcag aggaacccct caccgccacc      2700
ctgtcccagg cggcctttcc ccgaggcccg agggtcagat cctggggcca cctcgaggat      2760
ttctcacacc tgcccagcca cccccagctt ttcaggtgat accggagggt gggcgtgggg      2820
ctcctggcgc atccgagtcc ctccctggag tccccgaccg cggccgcccg gcccgacgct      2880
gccccgccgc cccgcagggc gggagccggc gctgcgggtg cgcccggcc agccgggcag       2940 ttgcgcaagt tgtgcttcgg cggctataag aggggcgggc aggcatggag ccccggaggg      3000
atcgaggaat cgcggcgcca gcagcggcga ggtaagtgcc cggctctctc ct              3052
```

<210> SEQ ID NO 3
<211> LENGTH: 3052
<212> TYPE: DNA
<213> ORGANISM: Bos taurus

<400> SEQUENCE: 3

```
gaattcaaca attctatttta tcaagaaatc tcccacaaat atactcacac tgtgctccaa      60
taagtacttt tgagtctatt aattaacaac attatgtatc taacattatg gttagattga     120
ttatggtgca tctgtgaaat gaaacatacg ctgactctaa aatgattggc acaatcctgt     180
gtattggtaa gaaattgtat tctagatata ctaggtgaaa gaagtgagat taataatggt     240
taaaattggg caatggtaca tggacatttg taatgccatt tttccttata agtgtattgt     300
ggagatttaa attttttccaa aaaaaaaaat gtggaggcag ggggcaagaa cattagtgtg     360
aataatatga cattatttaa atgcccttaa atatatattt tttaattaat ttatttatttt    420 tttctatgct gggtcttcat tgcaatgtgc aagcttctca ctgtggcagc ttctcctgtt     480
gtggagcata ggctccaggt gcccagggac tcagcggttg caacacatag gctctagagc     540
ttgggctcgg gagccgtgtc acacggcctt tgttgctccc agcatgtgga atcttcctca     600
accagggacc gatcccgcgt ccctgcactg gcaggcggat tctcatccac tgtaccacca     660
aggaaggcct gcacactttt ttttttaagg aaatggatat atgaaggaca gaaaagaat      720 atccatggaa ggatacacca taaactgaga agaacaacta cttctaggga aaaaaggact     780
ggggagagac tgagttttca tatctttgtt cctttttgaat tttaagaaaa ataatacatt    840
attctaacac aacattgtaa agcaattata cttcaataaa aaattaaaag taaaaatact     900
ttattatata ataatatata attataatat aatataaaca ttcagttcag ttcagttcac     960
ttcagtcgct cagtcgtgtc cgactctttt cgacccccatg aatcgcagca caccaggcct    1020
ccctgtccat caccaactcc cggagttcac ccagactcat agtaatatat aataatttat    1080
tttaaaataa ttattaatca acacgaaatg taaaaaatag gtaggtgatg ggtagatagg    1140
cagacgggca gtccacacac tcacatgtgg tctcaagtgc tacttggtgt tcaggcaata    1200
```

```
actctggtcc caatctgacc tctgacccct aaaaaggtga tggtaagaca agtaacctga    1260
ggctgccagg gcccctgcct atgagctaag actctgctta gaaccaagtt acaaagatgt    1320
tgcagacaag aaaaatttgg tcgtagtgga tgctactgcc tctatttgaa aaacaacaca    1380
aacatttccg ggggggggg gaggcggaga ggaggaaaga ttttcttcaa aatgtaattt     1440
cattgtagac acttctttaa aagaaacatt tctttatttg acagttccag gccttagttt    1500
cagcaggcag gatgtttagt cgcagcatga gaactcttag ctgcggcatg cgggacccag    1560
ttcagttccc tgaccagata tcgaacctgg ggccctgca tttggaagca gggagtctta     1620
gccactggac caccagggaa gtcccctgta gatgttttta tgaaaagcag aaaagcacaa    1680
agaagagctt aaagattcct gatcctactc ccaatagtga taatgtatat tttggtgtga    1740
gagtgtgtgt attgattgga atgtgtgtga tcagaaaaca cataccattt tataatccgt    1800
tctttccagc tcacaaaata aagttatttt cctacatcat taaatattac tttacaacat    1860 aattttaat gtgtgcatat tgctgctatg tgattttcaa taacttacta atttcctatg     1920
ctgaacattt agttgttgtc caacctttt agtggccatg taattataaa tcatggtcaa     1980
tgctaacaat ttctgacctc acaaacatat agtacaatat ccttcctttc ttcaatagat    2040
aattattaaa agcaaaacaa ccaggctcaa acaaagcaat tataaaatat ctttaaaaag    2100
acattgggta aaattcaaat gcagactagc tcatgatgtt aaagaattac tcttgtgtgg    2160
taatggtctt gtgatagaga tagaaatgct tccttatttt tcagataaac acttaagtat    2220
ttaaggatga aacgccctga tgtttgtaat ttgctttaga atatttagc caaaagaatt     2280 aatgatgcaa atatgcaaaa agagtacgtt aaacctaaat ttgcgatttt catttaaaaa    2340
tatatcttaa aaatgaaaat cttcgtgcaa cgcacggggc tatcaatgtg ggatacagat    2400
gtgaacaaaa cggacccgtg tgggactcgg cggagcacac agattttgcg ggagcacgtt    2460
cccgttagga agtctctgat gcaatacgac cggtgcccct caggacctgt gagactgact    2520
ttccttaccc ctccacacca tcatcaaggc aggtgtgatt ttccaggcca ggcctacggc    2580
cgggtttccc cggggccca gagccgtcgg gtcttgccgc ccagcggagc tggctgctcc     2640
ggcctcactg tcggggcgcc accgcccca gccggctcag aggaacccct caccgccacc     2700
ctgtcccagg cggcctttcc ccgaggcccg agggtcagat cctggggcca cctcgaggat    2760
ttctcacacc tgcccagcca cccccagctt ttcaggtgat accggagggt gggcgtgggg    2820
ctcctggcgc atccgagtcc ctccctggag tccccgaccg cggccgcccg gcccgacgct    2880
gccccgccgc cccgcagggc gggagccggc gctgcgggtg cgccccggcc agccgggcag    2940
ttgcgcaagt tgtgcttcgg cggctataag aggggcgggc aggcatggag ccccggaggg    3000
atcgaggaat cgcggcgcca gcagcggcga ggtaagtgcc cggctctctc ct            3052

<210> SEQ ID NO 4
<211> LENGTH: 3052
<212> TYPE: DNA
<213> ORGANISM: Bos taurus

<400> SEQUENCE: 4
gaattcaaca attctattta tcaagaaatc tcccacaaat atactcacac tgtgctccaa      60
taagtacttt tgagtctatt aattaacaac attatgtatc taacattatg gttagattga    120
ttatggtgca tctgtgaaat gaaacatacg ctgactctaa aatgattggc acaatcctgt    180
gtattggtaa gaaattgtat tctagatata ctaggtgaaa gaagtgagat taataatggt    240
taaaattggg caatggtaca tggacatttg taatgccatt tttccttata agtgtattgt    300
```

```
ggagatttaa attttttccaa aaaaaaaaat gtggaggcag ggggcaagaa cattagtgtg      360
aataatatga cattatttaa atgcccttaa atatatattt tttaattaat ttatttattt      420
tttctatgct gggtcttcat tgcaatgtgc aagcttctca ctgtggcagc ttctcctgtt      480
gtggagcata ggctccaggt gcccagggac tcagcggttg caacacacag gctctagagc      540
ttgggctcgg gagccgtgtc acacggcctt tgttgctccc agcatgtgga atcttcctca      600
accagggacc gatcccgcgt ccctgcactg gcaggcggat tctcatccac tgtaccacca      660
aggaaggcct gcactttttt tttttaagg aaatggatat atgaaggaca gaaaagaat       720 atccatggaa ggatacacca taaactgaga agaacaacta cttctaggga aaaaaggact      780
ggggagagac tgagttttca tatctttgtt ccttttgaat tttaagaaaa ataatacatt      840
attctaacac aacattgtaa agcaattata cttcaataaa aaattaaaag taaaaatact      900
ttattatata ataatatata attataatat aatataaaca ttcagttcag ttcagttcac      960
ttcagtcgct cagtcgtgtc cgactctttt cgacccatg aatcgcagca caccaggcct    1020
ccctgtccat caccaactcc cggagttcac ccagactcat agtaatatat aataatttat    1080
tttaaaataa ttattaatca acacgaaatg taaaaaatag gtaggtgatg ggtagatagg    1140
cagacgggca gtccacacac tcacatgtgg tctcaagtgc tacttggtgt tcaggcaata    1200
actctggtcc caatctgacc tctgacccct aaaaaggtga tggtaagaca agtaacctga    1260
ggctgccagg gcccctgcct atgagctaag actctgctta gaaccaagtt acaaagatgt    1320
tgcagacaag aaaaatttgg tcgtagtgga tgctactgcc tctatttgaa aaacaacaca    1380
aacatttccg ggggggggg gaggcggaga ggaggaaaga ttttcttcaa aatgtaattt    1440
cattgtagac acttctttaa aagaaacatt tctttatttg acagttccag gccttagttt    1500
cagcaggcag gatgtttagt cgcagcatga gaactcttag ctgcggcatg cgggacccag    1560
ttcagttccc tgaccagata tcgaacctgg ggccctgca tttggaagca gggagtctta    1620
gccactggac caccagggaa gtcccctgta gatgttttta tgaaaagcag aaaagcacaa    1680
agaagagctt aaagattcct gatcctactc ccaatagtga taatgtatat tttggtgtga    1740
gagtgtgtgt attgattgca atgtgtgtga tcagaaaaca cataccatt tataatccgt     1800 tctttccagc tcacaaaata aagttatttt cctacatcat taaatattac tttacaacat    1860 aattttaat gtgtgcatat tgctgctatg tgattttcaa taacttacta atttcctatg      1920
ctgaacattt agttgttgtc caaccttttt agtggccatg taattataaa tcatggtcaa    1980
tgctaacaat ttctgacctc acaaacatat agtacaatat ccttcctttc ttcaatagat    2040
aattattaaa agcaaaacaa ccaggctcaa acaaagcaat tataaaatat ctttaaaaag    2100
acattgggta aaattcaaat gcagactagc tcatgatgtt aaagaattac tcttgtgtgg    2160
taatggtctt gtgatagaga tagaaatgct tccttatttt tcagataaac acttaagtat    2220
ttaaggatga aacgccctga tgtttgtaat ttgctttaga atattttagc caaaagaatt    2280
aatgatgcaa atatgcaaaa agagtacgtt aaacctaaat ttgcgatttt catttaaaaa    2340
tatatcttaa aaatgaaaat cttcgtgcaa cgcacggggc tatcaatgtg ggatacagat    2400
gtgaacaaaa cggacccgtg tgggactcgg cggagcacac agattttgcg ggagcacgtt    2460
cccgttagga agtctctgat gcaatacgac cggtgccctt caggacctgt gagactgact    2520
ttccttaccc ctccacacca tcatcaaggc aggtgtgatt ttccaggcca ggcctacggc    2580
cgggtttccc cggggcccca gagccgtcgg gtcttgccgc ccagcggagc tggctgctcc    2640
ggcctcactg tcggggcgcc accgccccca gccggctcag aggaacccct caccgccacc    2700
```

-continued

```
ctgtcccagg cggcctttcc ccgaggcccg agggtcagat cctggggcca cctcgaggat    2760
ttctcacacc tgcccagcca cccccagctt ttcaggtgat accggagggt gggcgtgggg    2820
ctcctggcgc atccgagtcc ctccctggag tccccgaccg cggccgcccg cccgacgct     2880 gccccgccgc cccgcagggc gggagccggc gctgcgggtg cgccccggcc agccgggcag    2940
ttgcgcaagt tgtgcttcgg cggctataag aggggcgggc aggcatggag ccccggaggg    3000
atcgaggaat cgcggcgcca gcagcggcga ggtaagtgcc cggctctctc ct            3052
```

<210> SEQ ID NO 5
<211> LENGTH: 467
<212> TYPE: DNA
<213> ORGANISM: Bos taurus

<400> SEQUENCE: 5

```
gattccgccg cacctctccc caggggagtg cctttcatta ctgtcatttc tagacaatga     60
attgtctttg aggagatgat agccatggca gacagcaaat cttgttgtta tccgcatctg    120
aagacctgga tgcgggtggt aacggagcac gtgggtgttc tcggagatcg acgatgtgcc   180
acgtgtggtt tcttctgttt tcaggcccca gaagcccatc ccgggaagga aaatgcgctg   240
tggaccsctg tttcgattcc tgtggctttg gccctatctg tcttacgtgg aggctgtgcc   300
catctgcaag gtccaggatg acaccaaaac cctcatcaag acaattgtca ccaggatcaa   360
tgacatctca cacacggtag ggagggactg ggagacgagg tagaaccgtg gccatcccgt   420
gggggacccc agaggctggc ggaggaggct gtgcagcctt gcacagg                 467
```

<210> SEQ ID NO 6
<211> LENGTH: 467
<212> TYPE: DNA
<213> ORGANISM: Bos taurus

<400> SEQUENCE: 6

```
gattccgccg cacctctccc caggggagtg cctttcatta ctgtcatttc tagacaatga     60
attgtctttg aggagatgat agccatggca gacagcaaat cttgttgtta tccgcatctg    120
aagacctgga tgcgggtggt aacggagcac gtgggtgttc tcggagatcg acgatgtgcc   180
acgtgtggtt tcttctgttt tcaggcccca gaagcccatc ccgggaagga aaatgcgctg   240
tggaccsctg tttcgattcc tgtggctttg gccctatctg tcttacgtgg aggctgtgcc   300
catccgcaag gtccaggatg acaccaaaac cctcatcaag acaattgtca ccaggatcaa   360
tgacatctca cacacggtag ggagggactg ggagacgagg tagaaccgtg gccatcccgt   420
gggggacccc agaggctggc ggaggaggct gtgcagcctt gcacagg                 467
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ggcacaatcc tgtgtattgg taaga                                           25
```

<210> SEQ ID NO 8
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 8
gtccatgtac cattgcccaa ttt                                           23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ctttcaccta gtatatctag                                               20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tctttcacct agtatgtcta g                                             21

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aggtgcccag ggactca                                                  17

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caacaaaggc cgtgtgaca                                                19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
aagctctaga gcctatgt                                                 18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 14
caagctctag agcctgtgt                                                    19

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgtatattt tggtgtgaga gtgtgtgt                                          28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agctggaaag aacggattat aaaatggt                                          28

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cacacattcc aatcaa                                                       16

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
cacattgcaa tcaa                                                         14

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggctttggcc ctatctgtct tac                                               23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

```
cttgatgagg gttttggtgt ca                                                    22

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ccttgcagat ggg                                                              13

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ccttgcggat ggg                                                              13
```